US008173148B2

(12) United States Patent
Dadey et al.

(10) Patent No.: US 8,173,148 B2
(45) Date of Patent: *May 8, 2012

(54) STABILIZED POLYMERIC DELIVERY SYSTEM COMPRISING A WATER-INSOLUBLE POLYMER AND AN ORGANIC LIQUID

(75) Inventors: Eric Dadey, Furlong, PA (US); Mingxing Zhou, Fort Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 140 days.

This patent is subject to a terminal disclaimer.

(21) Appl. No.: 11/667,433

(22) PCT Filed: Nov. 10, 2005

(86) PCT No.: PCT/US2005/040855
§ 371 (c)(1),
(2), (4) Date: Jan. 3, 2008

(87) PCT Pub. No.: WO2006/053175
PCT Pub. Date: May 18, 2006

(65) Prior Publication Data
US 2008/0299168 A1    Dec. 4, 2008

Related U.S. Application Data

(60) Provisional application No. 60/626,780, filed on Nov. 10, 2004.

(51) Int. Cl.
*A61F 13/00* (2006.01)
*A61K 9/70* (2006.01)
*A61K 38/00* (2006.01)

(52) U.S. Cl. .......... 424/422; 424/426; 424/486; 514/1.1

(58) Field of Classification Search .................. 424/422, 424/426, 486; 514/1.1
See application file for complete search history.

(56) References Cited

U.S. PATENT DOCUMENTS

| | | | |
|---|---|---|---|
| 4,612,302 A | 9/1986 | Szabo et al. | |
| 4,652,441 A | 3/1987 | Okada et al. | |
| 4,666,704 A | 5/1987 | Shalati et al. | |
| 4,684,620 A | 8/1987 | Hruby et al. | |
| 4,853,371 A | 8/1989 | Coy et al. | |
| 4,917,893 A | 4/1990 | Okada et al. | |
| 4,938,763 A | 7/1990 | Dunn et al. | |
| 4,954,298 A | 9/1990 | Yamamoto et al. | |
| 5,061,492 A | 10/1991 | Okada et al. | |
| 5,278,201 A | 1/1994 | Dunn et al. | |
| 5,324,519 A | 6/1994 | Dunn et al. | |
| 5,330,767 A | 7/1994 | Yamamoto et al. | |
| 5,447,725 A | 9/1995 | Damani et al. | |
| 5,476,663 A | 12/1995 | Okada et al. | |
| 5,480,656 A | 1/1996 | Okada et al. | |
| 5,487,897 A | 1/1996 | Polson et al. | |
| 5,575,987 A | 11/1996 | Kamei et al. | |
| 5,631,020 A | 5/1997 | Okada et al. | |
| 5,631,021 A | 5/1997 | Okada et al. | |
| 5,643,607 A | 7/1997 | Okada et al. | |
| 5,651,990 A | 7/1997 | Takada et al. | |
| 5,702,716 A | 12/1997 | Dunn et al. | |
| 6,120,787 A | 9/2000 | Gustafsson et al. | |
| 6,143,314 A * | 11/2000 | Chandrashekar et al. | ..... 424/426 |
| 6,353,086 B1 * | 3/2002 | Kolstad et al. | ................ 528/354 |
| 2004/0001890 A1 | 1/2004 | Rosenblatt et al. | |
| 2004/0175429 A1 | 9/2004 | Alavattam et al. | |

FOREIGN PATENT DOCUMENTS

| | | |
|---|---|---|
| AU | 2005304435 | 6/2011 |
| EP | 0052510 A2 | 5/1982 |
| EP | 1430915 A1 | 6/2004 |
| WO | WO-90/11070 A1 | 10/1990 |
| WO | WO-2006053175 A3 | 5/2006 |

OTHER PUBLICATIONS

Garcia et al. ("Comparative degradation study of biodegradable microspheres of poly(DL-lactide-co-glycolide) with poly(ethyleneglycol) derivates,") J Microencapsulation 16(1):83-94, 1999.*
APAC Chemical Corp., record for citric acid, http://www.apacchemical.com/CitricAcid.htm, 2002, printed from the Internet on Nov. 1, 2010.*
Sahoo et al., ("Nanotech approaches to drug delivery and imaging," Drug Discovery Today 8(24):1112-1120, 2003.*
Berkland et al., "PLG microsphere size controls drug release rate through several competing factors," Pharm Res 20(7):1055-1062, 2003.*
Youan, "Microencapsulation of superoxide dismutase into biodegradable microparticles by spray-drying", *Drug Delivery*, 11(3), (May-Jun. 2004),209-214.
"Australian Application Serial No. 2005304435, First Examiner Report mailed May 17, 2010", 2 pgs.
"Australian Application Serial No. 2005304435, Office Action Response Filed Sep. 22, 2010", 29.
Australian Aplication No. 2005304435, Response filed Dec. 24, 2010 to Second Examination Report dated Oct. 20, 2010, 23 pgs.
"Australian Aplication No. 2005304435, Second Examination Report mailed Oct. 20, 2010", 2 pgs.
"Canadian Application Serial No. 2,586,846, Request for Examination and Voluntary Amendment filed Nov. 3, 2010", 16 pgs.
"European Application Serial No. 05819495.2, Extended European Search Report mailed Nov. 15, 2010", 9 pgs.
"International Application Serial No. PCT/US05/40855, International Search Report mailed Aug. 7, 2006", 5 pgs.

(Continued)

*Primary Examiner* — Rosanne Kosson
(74) *Attorney, Agent, or Firm* — Schwegman, Lundberg & Woessner P.A.

(57) ABSTRACT

The invention relates to a delivery system for the sustained and controlled delivery of a group of bioactive agents. More particularly, the invention relates to a delivery system and a method for delivery of a bioactive agent containing a nucleophilic functional group by means of a biodegradable, sustained-release implant. The implant may be a preformed implant, microparticles or an in situ formed implant. The implant includes a biodegradable thermoplastic polymer, the bioactive agent having a nucleophilic group substituent and a stabilizing associate as well as other optional components. The combination of the stabilizing associate with the bioactive agent prevents and/or minimizes and/or lessens degradation of the thermoplastic polymer by the bioactive agent.

32 Claims, 4 Drawing Sheets

OTHER PUBLICATIONS

"International Application Serial No. PCT/US05/40855, Invitation to Pay Additional Fees mailed Apr. 14, 2006", 2 pgs.

"International Application Serial No. PCT/US05/40855, Written Opinion mailed Aug. 7, 2006", 9 pgs.

"Australian Application Serial No. 2005304435, Subsequent Examiner Report mailed Jan. 13, 2011", 2 pgs.

"Australian Aplication No. 2005304435, Response filed Feb. 2, 2011 to Third Examination Report dated Jan. 13, 2011", 6 pgs.

"European Application Serial No. 05819495.2, Response filed Jun. 14, 2011 to Extended European Search Report mailed Nov. 15, 2010", 12 pgs.

"European Application Serial No. 05819495.2, Response Filed Nov. 23, 2011 to Office Action mailed Jul. 14, 2011", 5 pgs.

"European Application Serial No. 05819495.2, Examination Notification Art. 94(3) mailed Jul. 14, 2011", 5.

\* cited by examiner

STABILIZED POLYMERIC DELIVERY SYSTEM COMPRISING A WATER-INSOLUBLE POLYMER AND AN ORGANIC LIQUID

RELATED APPLICATIONS

This application is a nationalization under 35 U.S.C. §371 of PCT/US2005/040855, filed 10 Nov. 2005 and published as WO 2006/053175 A2 on 18 May 2006, which claims priority under 35 U.S.C. §119(e) to U.S. Provisional Patent Application Ser. No. 60/626,780, filed 10 Nov. 2004, which applications and publications are incorporated herein by reference and made a part hereof.

FIELD OF THE INVENTION

The field of the invention relates to a delivery system for the sustained and controlled delivery to an animal of a group of bioactive agents. More particularly, the invention relates to a delivery system and a method for delivery of a bioactive agent containing a nucleophilic functional group by means of a biodegradable, sustained-release implant.

BACKGROUND OF THE INVENTION

Polymeric implants are useful as delivery systems for the sustained and controlled release of bioactive agents to animals, including humans. The implants may be preformed as polymeric solids or as pharmaceutical liquids in mechanical reservoirs. These kinds of implants are inserted into a patient's body by invasive, surgical procedures. However, these surgical procedures are uncomfortable and can be dangerous. Also they require further surgical intervention to remove the implant or reservoir after the pharmaceutical delivery is complete. For these reasons, implant technology has long concentrated upon biodegradable implants. However, many biodegradable implants require the invasive, surgical procedure to achieve the implantation. Recently, injectable, biodegradable implants have been developed that avoid the need for such surgical procedures. One such implant system is based upon microparticles while another is based upon implant formation in situ by injection of a flowable composition. Such flowable compositions may be composed of polymers that are liquid at ambient temperature but solidify upon heating (pluronics), solutions of polymer that coagulate upon contact with body fluid, or solutions of polymer that remain liquid but are so viscous that they do not readily disperse when injected.

The polymers for such controlled release implants have been a focus of research for years. Their biodegradability, release control, burst effect, solidification and additional characteristics have been improved through such research. Pluronics, polyesters, polyamides, polyethers and hybrids thereof are a few examples of these polymers. By far, the most popular polymer for use in a biodegradable implant is the polyester.

The polyester and its close relatives, the polyanhydride and polycarbonate are well-known and have been used in pharmaceutical application for many years. For example, polyglycolide is the polymeric material typically used for absorbable sutures. The biocompatibility of these polyesters is due in part to the fact that they are degraded by routine biochemical pathways and result in naturally occurring metabolic products.

The biodegradability of these polymers is based upon their ability to be hydrolyzed. In living tissue, their degradation occurs through cleavage of the ester or ester-like bond. This ester cleavage is facilitated by nucleophilic groups, such as amine groups, within the enzymatic site of an appropriate enzyme, by nucleophilic groups of blood serum molecules, and by nucleophilic compounds usually in the presence of water. This facile biodegradability is a significant benefit for medical use but the susceptibility also presents a problem.

A wide variety of bioactive agents that are suitable for delivery via biodegradable implants contain such nucleophilic groups. These bioactive agents include natural and synthetic peptides, polypeptides, proteins, nucleotides, oligonucleotides, polynucleotides and organic small molecules that have pharmacological and physiological activity. It is readily recognized that these molecules often contain one or more nucleophilic groups such as amine groups.

The presence of a nucleophilic functional group on the bioactive agent can lead to an interaction between the agent and the biodegradable polymer of the composition. Consequently, whenever the agent and biodegradable polymer are combined, that same degradation activity can occur through interaction of the agent upon the biodegradable polymer rather than solely through the interaction of living tissue with the biodegradable polymer. Such an interaction can affect either the physical or chemical character of the composition resulting in a loss of the advantages of a sustained and controlled delivery implant. This deleterious interaction can affect the character and stability of the composition before administration, can affect the formation of a consistent implant upon administration, and can affect the controlled and sustained release of the bioactive agent from the implant.

Therefore, there is a need to develop controlled release compositions that will prevent or minimize undesirable degradation of the controlled release polymer by the bioactive agent. A further need is the development of implant precursors and/or injectable implant compositions that of form stable and consistent implants for the delivery of bioactive agents. There is also a need to develop a controlled release composition that can be formulated and stored as a unified mixture of composition polymer and bioactive agent. Further, there is a need to develop such a unified composition which will provide implants with variable duration of controlled release of the bioactive agent.

SUMMARY OF THE INVENTION

These needs and others are met by the present invention. The invention is directed to a controlled release polymeric delivery system for administration of a nucleophilic bioactive agent. The delivery system may be formulated as an implantable monolithic material, microparticles, or a flowable composition. Degradation of the system polymer is avoided, minimized or lessened by combination of a stabilizing associate and the nucleophilic bioactive agent. According to the invention, the monolithic material, microparticle formulation and/or flowable composition is capable of forming a controlled release, biodegradable implant containing the nucleophilic bioactive agent when introduced into a body and/or tissue.

The monolithic material is formed outside the body and is a composition of a biocompatible, biodegradable thermoplastic polymer and the combination of the nucleophilic bioactive agent with the stabilizing associate. The monolithic material may be a single body solid or viscous gel that can be implanted by methods known in the art, such as by surgical intervention. The implantable monolithic material may also include non-polymeric compounds, and/or additives for controlling release such as rate release retarding agents, rate release acceleration agents, pore forming agents, plasticizers, organic solvents, encapsulation agents for encapsulating the bioactive agent, thermal gelling agents, burst effect reducing materials, hydrogels, polyhydroxyl materials, leaching agents, tissue transporting agents, or other similar additives or any combination thereof.

The microparticles are also formed outside the body and are compositions of biocompatible, biodegradable thermoplastic polymer, and the combination of the nucleophilic bioactive agent with the stabilizing associate. Microparticles may have a structure whereby all of the components are homogeneously distributed throughout, or a structure whereby some components form a core while others form a shell or coating. The latter structure is often termed microcapsules or microspheres. The microparticles may include non-polymeric compounds and/or additives for controlling release such as rate release retarding agents, rate release acceleration agents, pore forming agents, plasticizers, organic solvents, encapsulation agents for encapsulating the bioactive agent, thermal gelling agents, burst effect reducing materials, hydrogels, polyhydroxyl materials, leaching agents, tissue transporting agents, or other similar additives, or any combination thereof. Typically, the microparticles are mixed with an inert liquid, gel or solid carrier for placement as an implant in a body. Placement can be achieved by surgical intervention or by injection through a needle, cannula, tube, laproscope, probe, trocar or other delivery device.

The flowable composition is a preferred delivery system of the invention. It is composed of a biocompatible thermoplastic polymer, a biocompatible organic liquid, and the combination of the nucleophilic bioactive agent with the stabilizing associate. The flowable composition may optionally include non-polymeric compounds and additives for controlling release such as rate release retarding agents, rate release acceleration agents, pore forming agents, plasticizers, encapsulation agents for encapsulating the bioactive agent, thermal gelling agents, burst effect reducing materials, hydrogels, polyhydroxyl materials, leaching agents, tissue transporting agents, or other similar additives or any combination thereof. The flowable composition may be a viscous or non-viscous liquid, gel or flowable semisolid that moves as a fluid so that it may be injected through a needle, cannula, tube, laproscope, probe, or other delivery device. When the flowable composition of the invention is placed within living tissue, the composition transforms to an implant that remains in the selected location of the tissue. The implant may be a solid, a gel, a paste, a semisolid, or a viscous liquid.

In all delivery systems according to the invention, the bioactive agent may take the form of a free molecule, an organic or inorganic salt of the free molecule, or it may be complexed or covalently conjugated with a carrier agent, may be a pro-bioactive agent (prodrug form), or may be a multiform bioactive agent (multiple units of the bioactive agent either complexed or covalently bonded together). Any of these bioactive forms may also be contained within microparticles or microcapsules within either the monolithic material or the flowable composition.

A bioactive agent according to the invention may be any chemical compound that exhibits an effect upon living tissue when it and the living tissue come into contact such that it may be directly biologically active or it may be biologically active as a prodrug or metabolite. Organic small molecules, inorganic small molecules, peptides, oligopeptides, proteins, nucleotides, nucleosides, oligonucleotides, oligonucleosides, polynucleotides, polynucleotides, polynucleic acids or similar molecules constitute such chemical compounds.

According to the invention, the bioactive agent in any form will be substituted with a nucleophilic group including all forms of nucleophilic nitrogen groups. At least to some extent, the nucleophilic group will be capable of participating in ester, anhydride and carbonate group hydrolysis. A preferred embodiment of the invention involves bioactive agents having nitrogen groups such as an amine group, an amidine group, an imine group, a nitrogen-heteroaromatic group, a nitrogen-heterocyclic group, any other nitrogen containing group or any combination thereof as the nucleophilic group or groups. The nucleophilic nitrogen group or groups may be basic as in the free molecule or may be in salt form such as a monobasic C1 to C5 organic or inorganic acid salt including but not limited to acetic acid, benzoic acid, hydrochloric or sulfuric acid salt.

The organic small molecule may be an aliphatic, aromatic, heteroaromatic, cyclic, alicyclic, heterocyclic organic compound optionally containing one or more carboxylic acid, ester, lactone, anhydride, carbonate, carbamate, urea, amide, lactam, imine, amidine, enamine, imide, oxime, carbonyl, hydroxyl, enol, amine, ether, sulfide, sulfonyl, sulfoxyl, sulfonic acid, thioamide, thiol, thioacid, thioester, thiourea, acetal, ketal, halide, epoxy, nitro, nitroso, xanthate, ynamine group or any combination thereof wherein the optional substituents are compatible with the nucleophilic group of the organic small molecule.

The peptide according to the invention contains one or more nucleophilic side chains of either a natural or non-natural configuration and has a molecular weight of no more than about 5,000 daltons. The peptide will contain at least one amino acid unit having a side chain which may be substituted by an amine, imine, amidine, or other nitrogen containing group. The phrase "at least one" means that the peptide may also contain a multiple number of amino acid units having nitrogen containing side chain groups in any combination.

The oligopeptide according to the invention contains from about 10 to about 50 amino acid groups of either a natural or non-natural configuration. The oligopeptide will contain at least one amino acid unit having a nucleophilic side chain (with a multiple number of such units also being included by the phrase "at least one"). The nucleophilic side chain may be substituted by an amine, imine, amidine or any other nitrogen containing group.

The polypeptide according to the invention contains 50 or more amino acid groups of either a natural or non-natural configuration and has a molecular weight of at least about 4,500 daltons up to about 10 million daltons. The polypeptide will contain at least one amino acid unit having a nucleophilic side chain (with a multiple number of such units also being included by the phrase "at least one"). The nucleophilic side chain may be substituted by an amine, imine, amidine, or any other nitrogen containing group.

The nucleotides, nucleosides, oligonucleotides, oligo-nucleoside and polynucleic acids according to invention are biologically active compounds having nucleophilic capabilities. They will be substituted by a basic nitrogen group. These groups may appear as substituents on the heteroaromatic rings or as substituents on alkyl or alkenyl side chains bound to the heteroaromatic rings of these compounds.

The stabilizing associate conjugates, complexes, associates or otherwise interacts with the nucleophilic group or groups of the bioactive agent so as to block, minimize or lessen the nucleophilic group participation in ester, anhydride or carbonate hydrolysis. Upon combination of the stabilizing associate and nucleophilic bioactive agent, and their combination with the other components, the delivery system of the invention is formed and is capable of forming consistent and controllable implants. Preferably, the stabilizing associate is first combined with a bioactive agent to form a stabilized bioactive mixture.

To prepare the delivery system, the stabilized bioactive mixture is formed as described above. Then, that stabilized bioactive mixture is combined with the other components to form the delivery system. The combination of a stabilizing associate with the bioactive agent and the biodegradable, thermoplastic polymer forms a delivery system that is physically stable, physically stable prior to administration to a tissue and that forms consistent, controlled release implants upon administration to a tissue site.

According to the invention, the preferred stabilizing associate may be an organic compound having multi-carboxylic acid, sulfonic acid or phosphoric acid groups, or may be a monocarboxylic, monosulfonic or monophosphoric acid of at least 6 carbons in length. Additional stabilizing associates include carbonate, sulfate and phosphate partial esters of monohydroxy compounds, diols and polyols such as glucose, sucrose, glycerol, pentaerythritol and the like.

When the stabilizing associate has multiple acid groups, it is believed to complex or conjugate with the nucleophilic group or groups of the bioactive agent. This interaction is believed to block the nucleophilic activity of the bioactive agent. When the stabilizing associate is a monoacid, it forms a precipitate with the nucleophilic bioactive agent. The molecular weight of the monoacid and the identity of the nucleophilic bioactive agent determine whether or not a precipitate will form.

The biodegradable, thermoplastic polymer used in the delivery system according to the invention may be a polyester, polyanhydride or a polycarbonate. The polyester may be composed of residues derived from hydroxycarboxylic acids or composed of the combination of diacids and diols. The polyanhydride may be composed of residues of dicarboxylic acids. The polycarbonate may be composed of residues of diols and carbonic acid.

The invention is also directed to a method for use of the delivery system to provide controlled delivery of a bioactive agent to a mammal, including a human. The method involves administration of the delivery system to or within a body. The administration may be within a tissue, an organ, or any space within a body, e.g., subcutaneous space. The administration may be at a single site or at multiple sites within an organism. The administration may be performed by surgical intervention, trocar or other invasive technique for implantation of a monolithic material or microparticles, or by piercing the dermis with a hollow implement and passing the system through the implement, in the case of microparticles or the flowable system. A single implantation or multiple implantations may occur as may be prescribed for the particular bioactive agent involved. Preferably, the administration of the flowable composition is accomplished by a needle, cannula, laproscope, or other manipulatable device for injection or placement of flowable materials.

The present invention is also directed to the implant formed from the monolithic material, microparticles or flowable composition of the invention. The implant of the invention is composed of a thermoplastic material, a bioactive agent containing at least one nucleophilic functional group, a stabilizing associate, and optional additives and/or optional organic liquid or liquids.

An especially preferred delivery system according to the present invention, is a flowable composition composed of a biodegradable, biocompatible, thermoplastic polymer, an organic liquid in which the thermoplastic polymer is soluble, and a combination of a stabilizing associate, and a nucleophilic bioactive agent. The stabilizing associate preferably is a monocarboxylic acid of at least 6 carbons, or a polycarboxylic acid, especially preferably a polycarboxylic acid. The stabilizing associate and the bioactive agent are complexed, conjugated or formed as an intimate mixture before their combination with the thermoplastic polymer and organic liquid. The preferred polycarboxylic acid according to this preferred embodiment of the invention contains two, three, four or more carboxylic acid groups and from two to twenty carbons wherein the number of carbons is chosen as appropriate for the number of carboxylic acid groups present. Sulfonic or phosphonic acid groups can be substituted for the carboxylic acid groups also. The preferred thermoplastic polymer is a polyester.

DEFINITIONS

Figure 1:
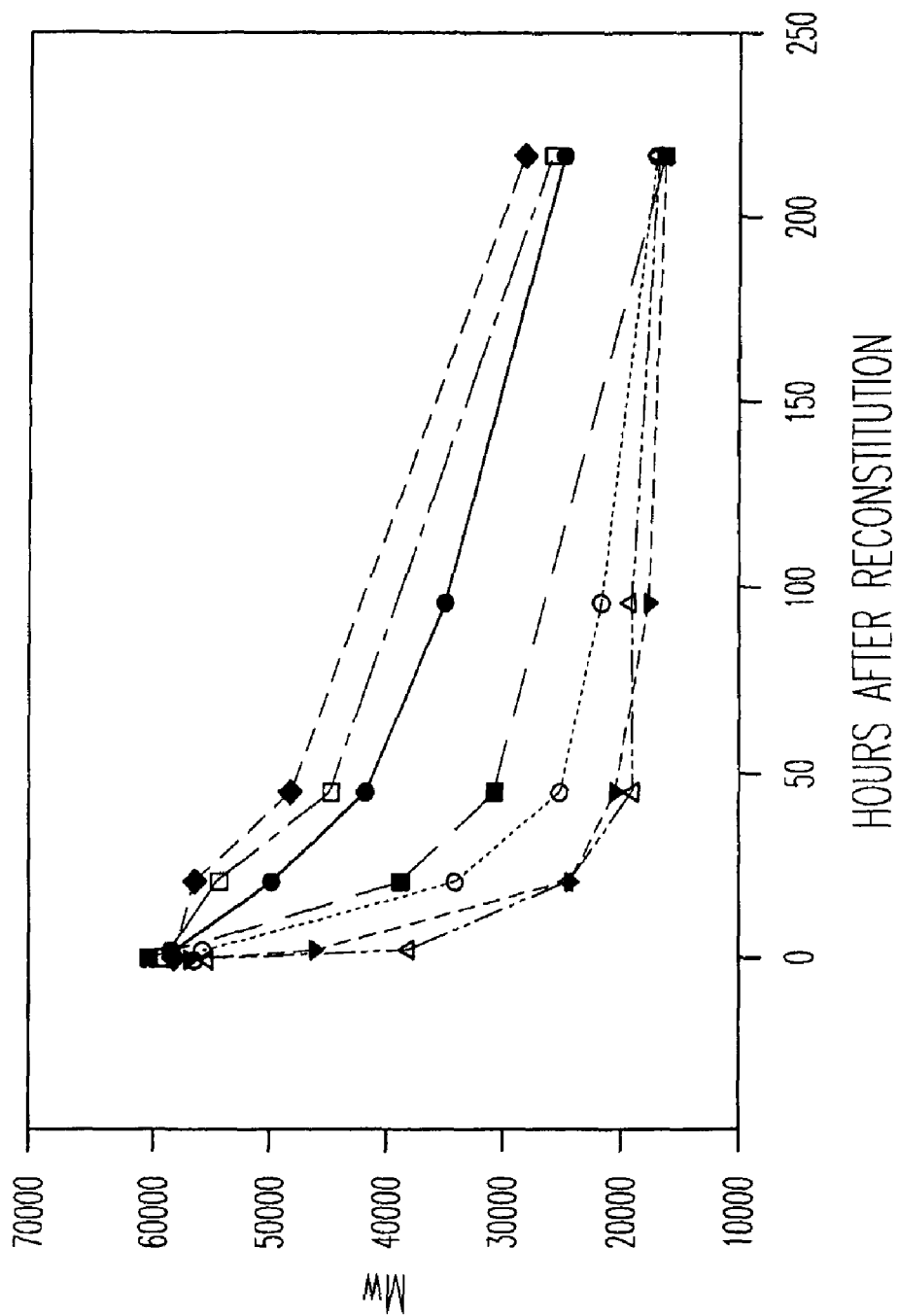
FIG. 1 is a graph showing the molecular weight degradation, over time, of polylactide-glycolide in the presence of octreotide acetate as a function of varying concentrations of citric acid.

The words and phrases presented in this patent application have their ordinary meanings to one of skill in the art unless otherwise indicated. Such ordinary meanings can be obtained by reference to their use in the art and by reference to general and scientific dictionaries such as Webster's New World Dictionary, Simon & Schuster, publishers, New York, N.Y., 1995; The American Heritage Dictionary of the English Language, Houghton Mifflin, *Boston Mass.,* 1981; Hawley's Condensed Chemical Dictionary $14^{th}$ edition, I. Sax, editor, Wiley Europe, 2002.

The following explanations of certain terms are meant as illustrative rather than exhaustive. These terms have their ordinary meanings given by usage in the art and in addition include the following explanations.

The term "amine group" refers to the group —$NR^1R^2$ wherein the R substituents individually are hydrogen or any alkyl, alkenyl, alkynyl, arylalkyl, alkaryl, heteroaryl or cyclic or heterocyclic group of 1 to 20 carbons each with optional oxygen and/or nitrogen substitutions.

The term "imine" refers to the group —$C{=}NR^1$ wherein the R substituent is defined as given above for the amine group.

The term "amidine" refers to the group $C({=}NR^1)NR^2R^3$ wherein the R substituents are defined as given above for the substituents of the amine group.

The term "heteroaromatic" refers to any aromatic compound or moiety containing a nitrogen and carbons in the nucleus of the heteroaromatic structure. A heteroaromatic compound exhibits aromaticity such as that displayed by a pyridine, pyrimidine, pyrazine or indole.

The term "heterocyclic" refers to any cyclic organic compound containing one or more nitrogen atoms in its cyclic structure. A heterocyclic compound may be saturated or unsaturated but is not aromatic.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propoargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C1-C6)alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "peptide" describes a sequence of 2 to about 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term polyester refers to polymers containing monomeric repeats, at least in part, of the linking group: —OC(=O)— or —C(=O)O—.

The term polyanhydride refers to polymers containing monomeric repeats, at least in part, of the linking group —C(=O)—O—C(=O)—.

The term polycarbonate refers to polymers containing monomeric repeats, at least in part, of the linking group —OC(=O)O—.

The term "saccharide" refers to any sugar or other carbohydrate, especially a simple sugar or carbohydrate. Saccharides are an essential structural component of living cells and source of energy for animals. The term includes simple sugars with small molecules as well as macromolecular substances. Saccharides are classified according to the number of monosaccharide groups they contain.

The term "polymer" means a molecule of one or more repeating monomeric residue units covalently bonded together by one or more repeating chemical functional groups. The term includes all polymeric forms such as linear, branched, star, random, block, graft and the like. It includes homopolymers formed from a single monomer, copolymer formed from two or more monomers, terpolymers formed from three or more polymers and polymers formed from more than three monomers. Differing forms of a polymer may also have more than one repeating, covalently bonded functional group.

The term "thermoplastic" as applied to a polymer means that the polymer repeatedly will melt upon heating and will solidify upon cooling. It signifies that no or only a slight degree of cross-linking between polymer molecules is present. It is to be contrasted with the term "thermoset" which indicates that the polymer will set or substantially cross-link upon heating or upon application of a similar reactive process and will then no longer undergo melt-solidification cycles upon heating and cooling.

The term "biocompatible" means that the material, substance, compound, molecule, polymer or system to which it applies will not cause severe toxicity, severe adverse biological reaction, or lethality in an animal to which it is administered at reasonable doses and rates.

DETAILED DESCRIPTION OF THE INVENTION

Drug delivery systems embody many forms and techniques for transport of drugs. Among the most convenient are those that constitute polymeric implants. They release the drug over time and do not require elaborate mechanical devices or semipermanent indwelling catheters for operation. These polymeric implants can be formulated as implantable monolithic materials, microparticles or flowable compositions to name a few. A difficulty with all, however, is the susceptibility of the polymer matrix toward accelerated degradation.

Biodegradable polymers used in typical drug delivery systems are metabolized by enzymatic and hydrolytic pathways. These metabolic pathways are based upon cleavage of the polymeric linking group joining the monomeric units of the polymer. For example, a common polymer used in delivery systems, the polyester, is metabolized by cleavage and/or hydrolysis or the ester group linking the monomeric units of the polymer.

The biodegradability is of great benefit because the polymer is naturally eliminated from the body, does not require post-delivery intervention for removal, and is typically based upon naturally occurring components. However, this biodegradability also presents a problem. The metabolic pathways can be mimicked chemically such that the biodegradable polymer can be degraded by ex vivo hydrolysis of the group or groups linking the monomeric units together as the polymer. For example, a polyester can be easily hydrolyzed by its mixture with a basic medium.

As a result, formulations of biodegradable delivery systems containing nucleophilic bioactive agents often have short shelf lives, low biological activity and undesirable side product contamination. Irrespective of the specific kind of delivery system involved, be it a preformed monolithic implant, microparticles or a flowable composition, these side effects are prevalent.

According to the invention, it has been surprisingly discovered that combining a nucleophilic bioactive agent with a stabilizing associate before contacting the nucleophilic bioactive agent with the biodegradable, thermoplastic polymer, substantially, and preferably essentially, blocks, minimizes or lessens the degradation of the biodegradable thermoplastic polymer caused by the nucleophilic bioactive agent. Although it is not intended to be a limitation or characterization of the invention, it is believed that the stabilizing associate at least lessens, and preferably minimizes the ability of the bioactive agent to act as a nucleophile. It is believed that this effect is achieved by complexing or otherwise tying up the lone pair electrons of the nucleophilic group or groups of the bioactive agent, thereby preventing them from participating in a nucleophilic attack upon the carbonyl carbon of the ester, anhydride or carbonate group of the thermoplastic polymer. If this participation were not blocked, the nucleophilic attack would facilitate addition of water to the ester, anhydride or carbonate linking groups of the thermoplastic polymer leading to its hydrolysis. Also surprisingly, simple neutralization of the nucleophilic group does not achieve such stabilization. For example, simple salt formation through use of acetic, hydrochloric or lactic acid neutralization of an oligopeptide having amine side chains from arginine and/or lysine residues does not minimize or eliminate the polymer degradation caused by the amine side chains, when the oligopeptide salt and polymer are combined. Consequently, complexation or otherwise insulating the nucleophilic group rather than simple neutralization provides an effective way to prevent, minimize or lessen polymer degradation.

The delivery system of the present invention may adopt any of a number of embodiments including a monolithic material, a microparticle formulation and a flowable composition. Each of these embodiments is designed for implantation. While the monolithic material is a preformed solid or gel that is implanted by surgery such as incision and suture or a trocar, the microparticle formulation is composed of microparticles in a liquid and the flowable composition is a solution or dispersion of components in an organic liquid. The microparticle formulation and the flowable composition are implanted by delivery to tissue through a hollow delivery device, such as a needle, cannula, tube, probe or the like.

The preferred embodiment of the delivery system according to the invention is the flowable composition. Unlike the monolithic material and microparticles, there are no preformed solids in the flowable composition. Consequently, the composition from which the implant is formed is easily prepared. Further, the composition may be easily injected as a controlled dose form within a tissue in a body. There is no problem involving settling as there is with microparticles. Also, there is no problem with infection as sometimes occurs with monolithic materials. Nevertheless, the present invention includes these three embodiments of the biodegradable delivery system as well as any other biodegradable delivery system that involves a hydrolysable polymer and a nucleophilic bioactive agent.

The monolithic material according to the invention may be formed from a mixture of at least the biodegradable thermoplastic polymer, the nucleophilic bioactive agent, the stabilizing associate. Additional components discussed below may also be present. The monolithic material is a preformed implant and may be a solid or shape retaining gel. The mixture may be combined in a fashion that will render the monolithic material homogeneous throughout, or that will produce a core and shell configuration such as in a capsule.

To produce a homogeneous monolithic material, an intimate admixture of the components is prepared, cast into forms and allowed to set to form the monolithic material ready for implantation. The core and shell monolithic material is formed in the same fashion by first casting the core as a homogeneous mixture of components and then in a second step, casting a shell of biodegradable thermoplastic polymer around the core. Through pressure, temperature, extrusion and the like, the components can be formed into the monolithic material as a solid or shape-retaining gel. For example, form casting can be accomplished by pressure molding, temperature (melt) molding, extrusion and the like into shaped molds. Sheets, plugs, cylinders, elliptical, spherical, oval shapes, capsule shapes and the like can also be cast or otherwise formed in this manner as the monolithic material. The size of the monolithic material may be any that will accommodate the desired amount of bioactive agent, be reasonably insertable into a patient and be reasonable to handle. Typical sizes range from 1 mm to 20 cm in length and 1 mm to about 5 cm in width. The techniques for forming pre-implant monolithic materials are known in the art. See for example, U.S. Pat. Nos. 3,442,871; 3,463,158; 3,773,919; 3,887,699; 4,161,948; 4,631,188; 4,767,628; the disclosures of which are incorporated herein by reference.

To facilitate combination of the components of the mixture, an organic solvent for all may be added. The solvent may be minimal so that a semi-solid mixture is achieved or the solvent may be of a significant concentration so that a solution or dispersion is achieved. Preferably, the solvent can be removed by evaporation, vacuum treatment or another similar technique to yield the monolithic material The microparticles according to the invention are solid or shape retaining gel particles of a dimension small enough that they will not cause emboli formation in the blood vessels of a mammal. Typically, the microparticle size ranges from about 0.01 micron to about 1000 microns, preferably from about 0.1 microns to about 100 microns, more preferably from about 0.1 micron to about 10 microns. The components of the microparticles include the biodegradable thermoplastic polymer, nucleophilic bioactive agent and stabilizing associate. Like the monolithic material, the microparticles may be homogeneous throughout or may be of a core and shell structure.

The microparticles may be formed by spray drying a mixture of the thermoplastic polymer, an organic solvent, a nucleophilic bioactive agent and the stabilizing associate. Additional components discussed below may also be present. Alternatively, a coassertive process may be used whereby a solution of the microparticle components in an organic solvent is dropwise contacted with a non-solvent for the thermoplastic polymer. The resulting coalesced droplets are filtered, the polymer solvent removed by heat and/or vacuum evaporation to form homogeneous microparticles. The microparticles may be used in this form or they may be coated with a shell of the biodegradable thermoplastic polymer to form microcapsules. These techniques are well-known in the art. See for example, U.S. Pat. Nos. 4,849,228; 5,330,767; 5,814,342; the disclosures of which are incorporated herein by reference.

The preferred flowable composition of the present invention is a combination of at least the biodegradable thermoplastic polymer, the nucleophilic bioactive agent, the stabilizing associate and an organic liquid. The components of the flowable composition are at least substantially soluble or dispersible in the organic liquid and all are biocompatible. Upon placement into living tissue, contact between the flowable composition and body fluids causes formation of a single body, controlled release implant within the tissue. The bioactive agent is substantially contained within the implant and is released gradually.

As mentioned, the flowable composition of the invention undergoes a transformation in situ to a solid, gel, semisolid, or viscous liquid when it is placed within tissue. The transformation occurs as the organic liquid dissipates from the composition and the thermoplastic polymer coagulates, precipitates or gels as body fluid contacts the implanted flowable composition. The transformation may occur slowly over a long period of time such as weeks or months, or may occur rapidly within seconds or minutes. The transformation depends upon a number of factors including but not limited to the body fluid solubilities, the hydrophilicities, hydrophobicities and hydrogelation of the thermoplastic polymer, the solubility of the organic liquid in body fluid, the physical properties of the bioactive agent, the selection and concentration of the stabilizing additive, and the optional additives.

More preferably, when the flowable composition is brought into contact with an aqueous environment, such as body fluids which typically surround tissues or organs in an organism, the organic liquid dissipates or disperses with dispatch into the body fluid and the substantially insoluble thermoplastic polymer facilely precipitates or coagulates to form a solid or gel matrix or implant. The incorporated bioactive agent is substantially trapped or encapsulated within the matrix as the implant forms. Once the solid implant is formed, the bioactive agent can be released from the matrix by diffusion or dissolution from within the matrix and/or the degradation of the matrix.

Upon implantation at the delivery site, the embodiments of the invention establish an implant incorporating the bioactive agent. The implant is primarily a polymer matrix and has the physical form of a single body solid, gel, semi-solid or viscous liquid. As the polymer matrix biodegrades and/or bioerodes, the bioactive agent is released from the matrix into the adjacent tissue and fluids. Also, the bioactive agent can be released from the polymer matrix by diffusion into the surrounding tissue and fluid.

The release of the nucleophilic bioactive agent from the polymeric matrix of the implant according to the invention occurs in a controlled fashion over a sustained time period. Through variations in selection of the components and their concentrations within the polymeric matrix, the rate of release of a bioactive agent and the duration of the release may be modified and predicted. For example, the release of the bioactive agent from the matrix may be varied by the solubility of the bioactive agent in water, the distribution of the bioactive agent within the matrix, or the size, shape, porosity, solubility and biodegradability of the polymer matrix, among other factors. Also, the manner of making the implant will have some effect upon the rate and duration of release of the bioactive agent. For example, microparticles expose a greater implant surface area for release so that on a comparable weight basis, microparticles will release the bioactive agent faster than will the monolithic material or the implant formed from the flowable composition. Further, the implant will biodegrade over a predictable time period to eliminate the need for removal. For example, the polymer matrix may be formulated to degrade after an effective and/or substantial amount of the bioactive agent is released from the matrix.

The delivery system and the resultant implant contain the bioactive agent in an amount effective to provide a desired biological, physiological, pharmacological, and/or therapeutic effect, optionally according to a desired release profile, and/or time duration of release. It is further preferred that the bioactive agent is included in the polymer matrix in an amount effective to provide an acceptable solution or dispersion viscosity.

The Bioactive Agent

The implants of the invention provide a platform for controlled, sustained delivery of bioactive agents to adjacent or distant body tissues and organs. The bioactive agents are capable of providing local or systemic biological or physiological activity in an animal, including a human, and are capable of being released from the implant matrix into surrounding body tissue.

According to the present invention, the bioactive agent will contain at least one functional nucleophilic group. (As used herein, the terms "bioactive agent" and "nucleophilic bioactive agent" have the same meaning: a bioactive agent containing at least one functional nucleophilic group.) A nucleophilic group can be characterized as a species with a pair of electrons that are available for bonding and in chemical reactions seeks the nucleus of an atom or the positive end of a polar molecule. The bioactive agents that contain a functional nucleophilic group include those molecules containing at least one nitrogen group.

According to the discovery of the invention, the presence of a functional nucleophilic group on the bioactive agent has been found to result in an interaction between the bioactive agent and the thermoplastic polymer in the delivery system. It has been discovered that this interaction can occur prior to, during, or after the administration of the delivery system to tissue. More specifically, it has been discovered that the thermoplastic polymer suitable for use in the invention can react with a bioactive agent containing a functional nucleophilic group in either free or salt form to result in a change of the thermoplastic polymer. These discoveries include such significant changes as a decrease in the molecular weight of the polymer and a resulting decrease in the viscosity and/or solid character of the delivery system and implant.

This change of the thermoplastic polymer character has been discovered to occur throughout the life of the delivery system irrespective of whether the system embodiment is a monolithic material, a microparticle formulation, or a flowable composition. Although the majority of these embodiments of the delivery system have a physical character of a solid or shape-retaining gel, the polymeric degradation caused by the bioactive agent has been discovered to occur within these embodiments as well as within the flowable composition. These solid or gel delivery system embodiments have been found to provide intimate contact between the nucleophilic bioactive agent and the thermoplastic polymer. Typically, they form a solid solution or gel solution. Also, the concentration of nucleophilic bioactive agent is typically substantial. Consequently, while freedom of molecular movement is restricted within these solid or gel embodiments, intimate contact of the nucleophilic agent and the thermoplastic polymer, and the presence of incidental water, such as from atmospheric vapor, enable polymer degradation just as has been discovered to occur in the flowable composition.

Changes of the thermoplastic polymer engendered by the nucleophilic bioactive agent both prior to, and after the placement of the delivery system into a tissue, have been discovered to introduce substantial, unpredictable variability in the character and behavior of the implants. It has been discovered that such implants show a substantial and non-controllable change in their ability to provide a controlled and sustained release of a bioactive agent. Consequently, control of the nucleophilic attack of nucleophilic bioactive agents upon the thermoplastic polymer of the delivery system of the invention is important. This control is accomplished by the combination of the nucleophilic bioactive agent and the stabilizing associate discussed separately below.

Bioactive agents containing a functional nucleophilic group include those bioactive agents containing at least one functional nitrogen group. The functional nitrogen group may be a primary, secondary, or tertiary amine, an amidine, an imine or a heteroaromatic group or heterocyclic group or any other nitrogen containing group or combination thereof. The functional amine group or groups of the bioactive agent may be in a free base form or may be in salt form with a simple organic monocarboxylic acid or a mineral acid.

One class of bioactive agents that contains a nucleophilic group and is included according to the invention is peptides, oligopeptides, polypeptides, and proteins having naturally occurring amino acid sequences, those having modified, naturally occurring sequences, (i.e., having naturally occurring sequences that have been chemically modified), those having synthetic or non-natural sequences, (i.e., having sequences of naturally occurring amino acids, the sequences of which do not occur in nature, or having sequences of non-naturally occurring amino acids, or combinations thereof), and those that are fragments of such sequences. These peptides, oligopeptides, polypeptides and proteins act to mimic, antagonize, activate, promote, enhance, block, initiate, stimulate or otherwise change, alter or affect biological physiology and function.

Peptides, oligopeptides, polypeptides, and proteins containing the amino acids lysine, arginine, histidine, and/or tryptophan contain a functional amine group. Peptides, oligopeptides, polypeptides, and proteins containing at least one lysine are of particular interest for the objectives of the invention.

Many naturally occurring peptides, oligopeptides, polypeptides, and proteins act as bioactive agents in animals. These include the number of peptide hormones synthesized by animals. Many of these molecules may be isolated or synthesized and re-introduced to animals as bioactive agents. In addition, there are many synthetic peptides, oligopeptides, polypeptides, and proteins that can be used as bioactive agents when administered to an animal, including a human subject. The delivery system of the present invention is suitable as a platform to provide naturally occurring, or modified naturally occurring, or synthetic/non-natural, or fragments of, peptides, oligopeptides, polypeptides, and proteins that can act as bioactive agents.

Examples of suitable, naturally occurring peptides, oligopeptides, polypeptides, and proteins containing amine or amidine side chains include the hypothalamic factors such as corticoliberin, folliberin, gonadoliberin, luliberin, melanoliberin, prolactoliberin, prolactostatin, and somatostatin. Examples of pituitary and related hormones include corticotropin, gonadotropin, glumitocin, lipotropin, ocytocin, prolactin, thyrotropin, vasopressin, and vasotocin. Other peptide hormones include brakykinin (kinin-9), calcitonin, gastrin, glucagon, proangiotensin, secretin, somatomedin, glucagon-like peptide (GLP-1 and GLP-2), and parathyrin [1-34].

Peptides for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, W E; Schuler, M; Peschel, C.; Huber, C.; Interleukins. Clinical pharmacology and therapeutic use. Drugs. 48(5):667-77, 1994 Nov.) and cytokines (referenced in Peters, M.; Actions of cytokines on the immune response and viral interactions: an overview. Hepatology. 23(4):909-16, 1996 Apr.).

Enkephlin and analogs, agonists and antagonists can be used to treat AIDS, ARC, and cancer, pain modulation, Huntington's, Parkinson's diseases.

LHRH and analogs, agonists and antagonists can be used to treat prostatic tumors and reproductive physiopathology, including breast cancer, and infertility.

Peptides and peptidomimetics that target crucial enzymes, oncogenes or oncogene products, tumor-suppressor genes and their products, growth factors and their corresponding receptors can be used to treat cancer. Examples of these peptides are described in Unger, C. Current concepts of treatment in medical oncology: new anticancer drugs. Journal of Cancer Research & Clinical Oncology. 122(4):189-98, 1996.

Neuropeptide Y and other pancreatic polypeptides, and analogs, agonists and antagonists can be used to treat stress, anxiety, depression and associated vasoconstrictive activities.

Gluco-incretins, including gastric inhibitory polypeptide, glucose-dependent insulinotropin polypeptide and glucagon-like polypeptide-1 and analogs, agonists and antagonists can be used to treat Type II diabetic hyperglycaemia.

Atrial natriuretic factor and analogs, agonists and antagonists can be used to treat congestive heart failure.

Integrin and analogs, agonists and antagonists can be used to treat osteoporosis, scar formation, bone synthesis, inhibition of vascular occlusion, and inhibition of tumor invasion and metastasis.

Glucagon, glucagon-like peptide 1 and analogs, agonists and antagonists can be used to treat diabetes cardiovascular emergencies.

Antithrombotic peptides and analogs, agonists and antagonists can be used to treat cardiovascular and cerebrovascular diseases. Examples of these peptides RGD, D-Phe-Pro-Arg and others named are described in Ojima I.; Chakravarty S.; Dong Q. Antithrombotic agents: from RGD to peptide mimetics. Bioorganic & Medicinal Chemistry. 3(4):337-60, 1995.

Cytokines/interleukins and analogs, agonists and antagonists can be used to treat inflammatory disease, immune response dysfunction, hematopoiesis, mycosis fungoides, aplastic anemia, thrombocytopenia, and malignant melanoma. Examples of these peptides are Interleukins, referenced in Aulitzky et al. and Peters et al.

Endothelin and analogs, agonists and antagonists can be used to treat arterial hypertension, myocardial infarction, congestive heart failure, atherosclerosis, shock conditions, renal failure, asthma and vasospasm.

Natriuretic hormones and analogs, agonists and antagonists can be used to treat cardiovascular disease and acute renal failure. Examples of these peptides are named and described in Espiner, E. A.; Richards, A. M.; Yandle, T. G.; Nicholls, M. G.; Natriuretic hormones. Endocrinology & Metabolism Clinics of North America. 24(3):481-509, 1995.

Peptides that activate or inhibit tyrosine kinase, or bind to TK-activating or inhibiting peptides and analogs, agonists and antagonists can be used to treat chronic myelogenous and acute lymphocytic leukemias, breast and ovarian cancers and other tyrosine kinase associated diseases. Examples of these peptides are described in Smithgall, T E.; SH2 and SH3 domains: potential targets for anti-cancer drug design. Journal of Pharmacological & Toxicological Methods. 34(3):125-32, 1995.

Renin inhibitors analogs, agonists and antagonists can be used to treat cardiovascular disease, including hypertension and congestive heart failure. Examples of these peptides are described in Rosenberg, S. H.; Renin inhibition. Cardiovascular Drugs & Therapy. 9(5):645-55, 1995.

Angiotensin-converting enzyme inhibitors, analogs, agonists and antagonists can be used to treat cardiovascular disease, including hypertension and congestive heart failure.

Peptides that activate or inhibit tyrosine phosphorylases can be used to treat cardiovascular diseases. Examples of these peptides are described in Srivastava, A. K.; Protein tyrosine phosphorylation in cardiovascular system. Molecular & Cellular Biochemistry. 149-150:87-94, 1995.

Peptide based antivirals can be used to treat viral diseases. Examples of these peptides are described in Toes, R. E.; Feltkamp, M. C.; Ressing, M. E.; Vierboom, M. P.; Blom, R. J.; Brandt, R. M; Hartman, M.; Offringa, R.; Melief, C. J.; Kast, W. M.; Cellular immunity against DNA tumor viruses: possibilities for peptide-based vaccines and immune escape. Biochemical Society Transactions. 23(3):692-6, 1995.

Corticotropin releasing factor and peptide analogs, agonists and antagonists can be used to treat disease associated with high CRF, i.e., Alzheimer's disease, anorexia nervosa, depressive, glucagon disorders, arthritis, and multiple sclerosis.

Peptide agonists and antagonists of platelet-derived wound-healing formula (PDWHF) can be used as a therapy for donor tissue limitations and wound-healing constraints in surgery. Examples of these peptides are described in Rudkin, G. H.; Miller, T. A.; Growth factors in surgery. Plastic & Reconstructive Surgery. 97(2):469-76, 1996.

Fibronectin, fibrinopeptide inhibitors and analogs, agonists and antagonists can be used to treat metastasis (i.e., enzyme inhibition, tumor cell migration, invasion, and metastasis).

Chemokines (types of cytokine, including interleukin-8, RANTES, and monocyte chemotactic peptide) analogs, agonists and antagonists can be used to treat arthritis, hypersensitivity, angiogenesis, renal disease, glomerulonephritis, inflammation, and hematopoiesis.

Neutral endopeptidase inhibitors and analogs, agonists and antagonists can be used to treat hypertension and inflammation. Examples of these peptides are described in Gregoire, J. R; Sheps, S. G; Newer antihypertensive drugs. Current Opinion in Cardiology. 10(5):445-9, 1995.

Substance P and analogs, agonists and antagonists can be used to treat immune system dysfunction, pain transmission/perception and in autonomic reflexes and behaviors.

Alpha-melanocyte-stimulating hormone and analogs, agonists and antagonists can be used to treat AIDS, rheumatoid arthritis, and myocardial infarction.

Bradykinin (BK) and analogs, agonists and antagonists can be used to treat inflammatory diseases (edema, etc), asthma, allergic reactions (rhinitis, etc), anesthetic uses, and septic shock.

Secretin can be used to treat cardiovascular emergencies.

GnRH and analogs, agonists and antagonists can be used to treat hormone-dependent breast and prostate tumors.

Somatostatin and analogs, agonists and antagonists can be used to treat gut neuroendocrine tumors.

Gastrin, Gastrin Releasing Peptide and analogs, agonists and antagonists can be used as an adjuvant to chemotherapy or surgery in small cell lung cancer and other malignancies, or to treat allergic respiratory diseases, asthma and allergic rhinitis.

Laminin-derived synthetic peptides analogs, agonists and antagonists can be used to treat tumor cell growth, angiogenesis, regeneration studies, vascularization of the eye with diabetes, and ischemia. Examples of these peptides are described in Kleinman, H. K.; Weeks, B. S.; Schnaper, H. W.; Kibbey, M. C.; Yamamura, K.; Grant, D. S; The laminins: a family of basement membrane glycoproteins important in cell differentiation and tumor metastases. Vitamins &Hormones. 47:161-86, 1993.

Defensins, corticostatins, dermaseptins, mangainins, and other antibiotic (antibacterial and antimicrobial) peptides and analogs, agonists and antagonists can be used to treat infections, tissue inflammation and endocrine regulation.

Vasopressin and analogs, agonists and antagonists can be used to treat neurological disorders, stress and Diabetes insipidus.

Oxytocin and analogs, agonists and antagonists can be used to treat neurological disorders and to induce labor.

ACTH-related peptides and analogs, agonists and antagonists can be used as neurotrophic, neuroprotective, and peripheral demyelinating neuropathy agents.

Amyloid-beta peptide and analogs, agonists and antagonists can be used to treat Alzheimer's disease.

Epidermal growth factor, receptor, and analogs, agonists and antagonists can be used to treat necrotizing enterocolitis, Zollinger-Ellison syndrome, gastrointestinal ulceration, colitis, and congenital microvillus atrophycarcinomas.

Leukocyte adhesion molecules and their ligands, and analogs, agonists and antagonists can be used to treat atherosclerosis, inflammation. Examples of these peptides are described in Barker, J. N.; Adhesion molecules in cutaneous inflammation. Ciba Foundation Symposium. 189:91-101.

Major histocompatibility complex (MHC) binding peptides and analogs, agonists and antagonists can be used to treat autoimmune, immunodysfunctional, immunomodulatory diseases and as well as used for their corresponding therapies. Examples of these peptides are described in Appella, E.; Padlan, E. A.; Hunt, D. F; Analysis of the structure of naturally processed peptides bound by class I and class II major histocompatibility complex molecules. EXS. 73:105-19, 1995.

Corticotropin releasing factor can be used to treat neurological disorders.

Neurotrophins (including brain-derived neurotrophic factor (BDNF), nerve growth factor, and neurotrophin 3) and analogs, agonists and antagonists can be used to treat neurological disorders.

Cytotoxic T-cell activating peptides can be used to treat infectious diseases and cancer. Examples of these peptides are described in: Chesnut R. W.; Sette, A.; Celis, E.; Wentworth, P.; Kubo, R. T.; Alexander, J.; Ishioka, G.; Vitiello, A.; Grey, H. M; Design and testing of peptide-based cytotoxic T-cell-mediated immunotherapeutics to treat infectious diseases and cancer. Pharmaceutical Biotechnology. 6:847-74, 1995.

Peptide immunogens for prevention of HIV-1 and HTLV-I retroviral infections can be used to treat AIDS. Examples of these peptides are described in Hart, M. K.; Palker, T. J.; Haynes, B F; Design of experimental synthetic peptide immunogens for prevention of HIV-1 and HTLV-I retroviral infections. Pharmaceutical Biotechnology. 6:821-45, 1995.

Galanin and analogs, agonists and antagonists can be used to treat Alzheimer's disease, depression, eating disorders, chronic pain, prevention of ischemic damage, and growth hormone modulation.

Tachykinins (neurokinin A and neurokinin B) and analogs, agonists and antagonists can be used to treat pain transmission/perception and in autonomic reflexes and behaviors.

RGD containing peptides can be used to treat various diseases involved with cell adhesion, antithrombotics, and acute renal failure.

Osteogenic growth peptide and analogs, agonists and antagonists can be used as treatment of systemic bone loss. Examples of these peptides are described in Bab IA. Regulatory role of osteogenic growth peptide in proliferation, osteogenesis, and haemopoiesis. Clinical Orthopedics & Related Research. (313):64-8, 1995.

Parathyroid hormone, parathyroid hormone related-peptide and analogs, agonists and antagonists can be used to treat diseases affecting calcium homeostasis (hypercalcemia), bone metabolism, vascular disease, and atherosclerosis.

Kallidin and analogs, agonists and antagonists can be used to treat tissue injury or inflammation and pain signaling pathological conditions of the CNS.

T cell receptor peptide vaccines and analogs, agonists and antagonists can be used in immunotherapy. Examples of these peptides are described in Brostoff, S W; T cell receptor peptide vaccines as immunotherapy. Agents & Actions—Supplements. 47:53-8, 1995.

Platelet-derived growth factor (PDGF) and analogs, agonists and antagonists can be used to treat non-neoplastic hyperproliferative disorders, therapy for donor tissue limitations and wound-healing constraints in surgery.

Amylin, calcitonin gene related peptides (CGRP) and analogs, agonists and antagonists can be used to treat insulin-dependent diabetes.

Vasoactive intestinal polypeptide and analogs, agonists and antagonists can be used to treat allergic respiratory diseases, asthma and allergic rhinitis, and nervous control of reproductive functions.

Growth hormone-releasing hormone and analogs, agonists and antagonists can be used to treat growth hormone deficiency and immunomodulation.

HIV protease inhibiting peptides can be used to treat AIDS. Examples of these peptides are described in Bugelski, P. J.; Kirsh, R.; Hart, T. K; HIV protease inhibitors: effects on viral maturation and physiologic function in macrophages. Journal of Leukocyte Biology. 56(3):374-80, 1994.

Thymopoietin active fragment peptides and analogs, agonists and antagonists can be used to treat rheumatoid arthritis and virus infections.

Cecropins and analogs, agonists and antagonists can be used as antibacterials.

Thyroid releasing hormone and analogs, agonists and antagonists can be used to treat spinal cord injury and shock.

Erythropoietin and analogs, agonists and antagonists can be used to treat anemia.

Fibroblast growth factor (FGF), receptor and analogs, agonists and antagonists can be as stimulation of bone formation, as well as used as a treatment for Kaposi's sarcoma, neuron regeneration, prostate growth, tumor growth inhibition, and angiogenesis.

Stem cell factor and analogs, agonists and antagonists can be used to treat anemias.

GP120, GP160, CD4 fragment peptides and analogs, agonists and antagonists can be used to treat AIDS.

Insulin-like growth factor, receptor, and analogs, agonists and antagonists can be used to treat breast and other cancers, noninsulin-dependent diabetes mellitus, cell proliferation, apoptosis, hematopoiesis, AIDS, growth disorders, osteoporosis, and insulin resistance.

Colony stimulating factors (granulocyte-macrophage colony-stimulating factor, granulocyte colony-stimulating factor, and macrophage colony-stimulating factor and analogs, agonists and antagonists can be used to treat anemias.

Kentsin and analogs, agonists and antagonists can be used for immunomodulation.

Lymphocyte activating peptide and analogs, agonists and antagonists can be used for immunomodulation. Examples of these peptides are described in Loleit, M.; Deres, K.; Wiesmuller, K. H.; Jung, G.; Eckert, M.; Bessler, W. G; Biological activity of the *Escherichia coli* lipoprotein: detection of novel lymphocyte activating peptide segments of the molecule and their conformational characterization. Biological Chemistry Hoppe-Seyler. 375(6):407-12, 1994 Jun.

Tuftsin and analogs, agonists and antagonists can be used for immunomodulation.

Prolactin and analogs, agonists and antagonists can be used to treat rheumatic diseases, systemic lupus erythematosus, hyperprolactemia.

Angiotensin II and receptor(s) and analogs, agonists and antagonists can be used to treat hypertension, hemodynamic regulation, neurological disorders, diabetic nephropathies, aortoarterities induced RVH, hyperaldosteronism, heavy metal induced cardiovascular effects, diabetes mellitus and thyroid dysfunction.

Dynorphin and analogs, agonists and antagonists can be used to treat neurological disorders, pain management, algesia, spinal cord injury and epilepsy.

Calcitonin, and analogs, agonists and antagonists can be used to treat neurological disorders, immune system dysfunction, calcium homeostasis, and osteoporosis.

Pituitary adenylate cyclase activating polypeptide can play a role in growth, signal transduction vasoactivity roles, exact role in diseases not determined yet.

Cholecystokinin and analogs, agonists and antagonists can be used to treat feeding disorders, panic disorders, and anti-opioid properties.

Pepstatin and analogs, agonists and antagonists can be used a pepsin and HIV protease inhibitor (AIDS).

Bestatin and analogs, agonists and antagonists can be used to treat muscular dystrophy, anticancer, antileukemia, immune response modulator, and acute non-lymphocytic leukemia.

Leupeptin and analogs, agonists and antagonists can be used as a protease inhibitor, exact role in diseases not determined yet.

Luteinizing hormone and releasing hormone and analogs, agonists and antagonists can be used as a infertility male contraceptive.

Neurotensin and analogs, agonists and antagonists can be used as a antipsychotic and analgesic agent.

Motilin and analogs, agonists and antagonists can be used as for the control of gastric emptying.

Insulin and analogs, agonists and antagonists can be used to treat diabetes.

Transforming growth factor (TGF) and analogs, agonists and antagonists can be used for cell proliferation and differentiation, cancer treatment, immunoregulation, therapy for donor tissue limitations, and wound-healing constraints in surgery.

Bone morphogenetic proteins (BMPs) and analogs, agonists and antagonists can be used as therapy for donor tissue limitations, osteogenesis, and wound-healing constraints in surgery.

Bombesin and analogs, agonists and antagonists can be used to prevent the proliferation of tumor cells, modulation of feeding, and neuroendocrine functions.

Glucagon, ☐egradati-like peptide 1 and analogs, agonists and antagonists can be used to treat diabetes cardiovascular emergencies.

Pancreastatin, chromogranins A, B and C and analogs, agonists and antagonists—conditions associated with inhibition of insulin secretion, exocrine pancreatic secretion and gastric acid secretion, and stimulation of ☐egradati secretion.

Endorphins and analogs, agonists and antagonists can be used to treat neurological disorders, alleviating pain, treatment of opioid abuse, obesity, and diabetes. Examples of these peptides are named and described in Dalayeun, J. F.; Nores, J. M.; Bergal, S.; Physiology of beta-endorphins. A close-up view and a review of the literature. Biomedicine & Pharmacotherapy. 47(8):311-20, 1993.

Miscellaneous opioid peptides, including (but not limited to) adrenal peptide E, alpha casein fragment, beta casomorphin, dermorphin, kyotorphin, metophamide neuropeptide FF (NPFF), melanocyte inhibiting factor, and analogues, agonists and antagonists can be used to treat neurological disorders, alleviating pain, as well as for the treatment of opioid abuse.

Vasotocin and analogues, agonists and antagonists can be used for clinical uses to be determined.

Protein kinase C and inhibitors and analogues, agonists and antagonists can be used to treat cancer, apoptosis, smooth muscle function, and Alzheimer's disease. Examples of these peptides are named and described in Philip, P. A.; Harris, A. L; Potential for protein kinase C inhibitors in cancer therapy. Cancer Treatment & Research. 78:3-27, 1995.

Amyloid, amyloid fibrin, fragments and analogues, agonists and antagonists can be used to treat neurodegenerative diseases and diabetes.

Calpain and other calmodulin-inhibitory proteins and analogues, agonists and antagonists can be used to treat neurodegenerative disorders, cerebral ischaemia, cataracts, myocardial ischaemia, muscular dystrophy and platelet aggregation.

Charybdotoxin, Apamin and analogues, agonists and antagonists can be used for treatment of neurodegenerative diseases and pain and cerebral ischemia.

Phospholipase A2 and receptor inhibiting/activating peptides and analogues, agonists and antagonists can be used to treat acute pancreatitis, pancreatic cancer, abdominal trauma, and inflammation, e.g., sepsis, infections, acute pancreatitis, various forms of arthritis, cancer, complications of pregnancy, and postoperative states.

Potassium channel activating and inhibiting proteins and analogues, agonists and antagonists can be used to treat various diseases. Examples of these peptides are described in Edwards, G.; Weston, A. H; Pharmacology of the potassium channel openers. Cardiovascular Drugs & Therapy. 9 Suppl 2:185-93, 1995 Mar.

IgG activators, inhibitors and analogues, agonists and antagonists can be used to treat autoimmune diseases and immune dysfunctions. Examples of these peptides are described in Mouthon, L.; Kaveri, S. V.; Spalter, S. H.; Lacroix-Desmazes, S.; Lefranc, C.; Desai, R.; Kazatchkine, M. D; Mechanisms of action of intravenous immune globulin in immune-mediated diseases. Clinical & Experimental Immunology. 104 Suppl 1:3-9, 1996.

Endotoxin and inhibitors and analogues, agonists and antagonists can be used for decreasing cardiac output, systemic hypotension, decreased blood flow and $O_2$ delivery to tissues, intense pulmonary vasoconstriction and hypertension, bronchoconstriction, increased permeability, pulmonary oedema, ventilation-to-perfusion inequalities, hypoxaemia, and haemoconcentration. Examples of these peptides are named and described in Burrell, R; Human responses to bacterial endotoxin. Circulatory Shock. 43(3): 137-53, 1994 Jul.

Substances which are capable of promoting growth and survival of cells and tissues or augmenting the functioning of cells, or metabolic precursors thereof are also useful biologically active agents, for example, a nerve growth promoting substance such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGP), insulin-derived growth factor (IGF-I, IGF-II), transforming growth factor alpha (TGF-I), transforming growth factor beta (TGF-θ), epidermal growth factor (EGF), fibroblast growth factor (FGF), or interleukin-1 (IL-1); an osteoinductive agent or bone growth promoting substance such as bone chips, or demineralized freeze-dried bone material; antineoplastic agents such as methotrexate, 5-fluorouracil, floxuridine, adriamycin, vinblastine, cisplatin, tumor-specific antibodies conjugated to toxins or tumor necrosis factor (TNF).

Other useful substances include hormones such as progesterone, testosterone, and follicle stimulating hormone (FSH) (birth control, fertility enhancement), insulin, or somatotrophins; antihistamines such as diphenhydramine, or chlorpheniramine; cardiovascular agents such as digitalis, nitroglycerine, papaverine, or streptokinase; anti-ulcer agents such as cimetidine hydrochloride, or isopropamide iodide; bronchodilators such as metaproternal sulfate, or aminophylline; vasodilators such as theophylline, niacin or minoxidil; central nervous system agents such as a tranquilizer, θ-adrenergic blocking agents, or dopamine; antipsychotic agents such as risperidone, olanzapine; narcotic antagonists such as naltrexone, naloxone or buprenorphine.

Analogues of peptide and protein hormones may be synthesized to be longer acting or show higher activity than the naturally occurring peptide. The composition of the present invention is suitable as a controlled release delivery system for such synthesized analogues. Examples include Exendin-3 and Exendin-4 which are analogues of GLP (glucagon-like peptide).

Another class of bioactive agents having a nucleophilic group is the nucleotides, oligonucleotides, polynucleotides and corresponding nucleosides and nucleic acids. These molecules have such bioactive functions as antiviral agents, antibacterial agents, anticancer agents, antisense agents, pcr probes and the like. Examples include AZT, aminouracil, carbovir, acyclovir, valacyclovir methotrexate, purine and pyrimidine nucleosides such as L-deoxynucleosides (the native forms are D-deoxynucleosides), their prodrug derivatives as β-L-2'deoxythymidine (LdT) and β-L-2'-deoxycytidine (LdC) are described in PCT patent applications WO00/09531 and WO 01/96353.

Bioactive agents as small molecules with nucleophilic groups include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

The biologically active agents also include androgen inhibitors, aminopolysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenyl propanolamine hydrochloride, caffeine, guaifenesin, peptides, polypeptides, proteins, amino acids, hormones, interferons, cytokines, and vaccines having nucleophilic groups.

Also included are peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent may further be a substance capable of acting as a stimulant, sedative, hypnotic, analgesic, anticonvulsant, and the like.

Examples of biologically active agents that are useful include substances capable of preventing an infection systemically in an animal or locally at the defect site, for example, anti-inflammatory agents such as hydrocortisone or prednisone; antibacterial agents such as penicillin, cephalosporins, bacitracin, tetracycline, doxycycline, gentamycin, quinolines, neomycin, clindamycin, kanamycin, or metronidazole; antiparasitic agents such as quinacrine, chloroquine, or vidarabine; antifungal agents such as nystatin; antiviral agents such as acyclovir, ribarivin, or interferons; analgesic agents such as acetaminophen, ibuprofen, naproxen, piroxicam, flurbiprofen, or morphine; local anesthetics such as cocaine, lidocaine, bupivacaine, and benzocaine; immunogens (vaccines) for stimulating antibodies against hepatitis, influenza, measles, rubella, tetanus, polio, and rabies; peptides such as leuprolide acetate (an LH-RH agonist), nafarelin, or ganirelix.

Other bioactive agents containing a nucleophilic group include antipsychotic agents such as ziprasidone, resperadone, and olanzepine; antimigraine agents such as sumatriptan and dihydroergotamine; analgesic agents such as morphine, oximorphone, bupivicaine, sufentanil, and fentanyl; narcotic antagonists such as naloxone and naltrexone; antineoplastic agents such as doxorubicin and mitocycin; and antimicrobial agents such as doxicyclin, amikacin, streptomycin, and ciprofloxacin.

In a preferred embodiment of the invention the bioactive agent containing a nucleophilic functional group is octreotide or octreotide acetate. Ocreotide or its salt form, octreotide acetate, is a synthetic analogue of the natural hormone somatostatin with similar but more prolonged pharmacological effects. It is a cyclic octapeptide and is known chemically as L-cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2→7)-disulfide; [R—(R*, R*)]. Preferably the concentration of the octreotide or octreotide acetate in the delivery system is from about 1% to about 25% by weight of the total delivery system, more preferably the concentration is from about 5% to about 15% by weight of the delivery system. Expressed as the delivered dose within an implant, preferably the dose of octreotide delivered is from about 1 mg to about 100 mg, more preferably from about 5 mg to about 50 mg.

Another preferred embodiment of the invention is a delivery system containing GHRP-1 (growth hormone releasing peptide). GHRP-1 is a seven amino acid peptide containing one lysine and one tryptophan. In a preferred embodiment the concentration of GHRP-1 in the delivery system is from about 50 mg/ml to about 150 mg/ml. Preferably the delivered amount of GHRP-1 to a human subject for a controlled release over a period of at least 30 days is from about 25 mg to about 150 mg, more preferably the delivered amount is from about 50 mg to about 100 mg.

The solubility of the bioactive agent in the delivery system components may be varied. The bioactive agent may be completely soluble in those components so as to provide a homogeneous delivery system. The bioactive agent may alternatively be insoluble in the delivery system components so as to form a suspension or dispersion with the delivery system. Further, the bioactive agent may be soluble in the delivery system components and delivery system may be formulated with an amount of bioactive agent that causes its saturation within the delivery system so that additional undissolved bioactive agent is present in suspension or dispersion.

Stabilizing Associate

The delivery system of the invention includes a stabilizing associate to combine or interact with the bioactive agent so as to stabilize the performance of the thermoplastic polymer. The addition of a stabilizing associate to the other delivery system components will produce a delivery system that has sufficient practical stability upon compounding to provide a physically consistent and controllable delivery system for placement into living tissue. The presence of a stabilizing associate provides a delivery system that upon placement into a tissue will provide consistent and controllable implants for the sustained release of the bioactive agents. More specifically, a stabilizing associate will serve to reduce at least to some extent the interaction between the thermoplastic polymer and a bioactive agent containing a nucleophilic functional group.

The effect of the presence of a stabilizing additive can be measured by the stability of the polymer average molecular weight after compounding the delivery system. Under the influence of the stabilizing additive, the delivery system may exhibit a lessening of polymer average molecular weight that is substantially lower than that exhibited by a corresponding system without the stabilizing additive. For example, without the stabilizing additive, a flowable composition may exhibit a decrease in polymer average molecular weight of up to 50 percent over a period of 10 to 20 hours. In the presence of the stabilizing additive, a flowable composition may exhibit a decrease in polymer average molecular weight of up to 15 percent over a period of 5 to 10 days. In other embodiments, the ultimate decrease in polymer average molecular weight may be similar for flowable compositions with and without the stabilizing additive but whereas the flowable composition without the stabilizing additive may achieve that polymer average weight reduction over a period of 1 to 2 days, the flowable composition with the stabilizing additive may achieve that polymer average weight reduction over a period of 2 to 3 weeks.

The effect can also be measured by a reduction of the initial burst of the bioactive agent from the implant placed in tissue. Further, the beneficial effect of the presence of a stabilizing associate can be measured by the controlled release over a sustained period of the bioactive agent from the implant placed in tissue.

Stabilizing associates suitable for the composition of the invention include organic carboxylic acids, phosphoric acids, and sulfonic acids. These organic acids include polyprotic acids and monoprotic acids having chain lengths greater than about 6 carbons such that the complex of bioactive agent and monoprotic acid stabilizing associate forms a precipitate. Surprisingly, monoprotic acids of less than 6 carbons in length do not act to prevent degradation of the thermoplastic polymer in the presence of the nucleophilic bioactive agent. Acetic acid, butyric acid and lactic acid are examples of such non-functioning monoprotic acids.

Suitable carboxylic organic acids include but are not limited to monocarboxylic acids of about 6 to 100 carbons, as well as dicarboxylic acids, tricarboxylic acids, tetracarboxylic acids and pentacarboxylic acids having from 2 to 100 carbons. These carboxylic acids may be saturated, unsaturated, aromatic (aryl or arylalkyl) and linear or branched in carbon structure; and may be unsubstituted by groups other than hydrogen or oxygen, or optionally substituted by such groups as halo, nitro, and the like. Specific examples include but are not limited to adipic acid, biotin, butyloctanoic acid, capric acid, caproic acid, caprylic acid, glutaric acid, citric acid, edetic acid, itaconic acid, fumaric acid, glucaric acid, malic acid, malonic acid, maleic acid, sebacic acid, oxalic acid, tartaric acid, undecanoic acid, undecylenic acid, pimelic acid, succinic acid, octadecanoic acid, oleic acid, linoleic acid, linolenic acid, lauric acid, palmitic acid, isostearic acid, 1,8-naphthalic dicarboxylic acid, phthalic acid, and similar mono or polycarboxylic acids. Suitable organic carboxylic acids may used alone or in combination. The monocarboxylic acids used according to the invention will form precipitates with the bioactive agent.

Suitable phosphoric organic acids include but are not limited to monophosphoric acids of about 6 to 100 carbons, as well as di phosphoric acids, tri phosphoric acids, tetraphosphoric acids and pentaphosphoric acids having from 2 to 100 carbons. These phosphoric organic acids may be saturated, unsaturated, aromatic and linear or branched in carbon structure; and may be unsubstituted by groups other than hydrogen or oxygen, or optionally substituted by such groups as halo, nitro, and the like. Partial phosphoric esters having at least one acidic phosphoric group are also included. The esterifying groups include alkyl of 1 to 10 carbons aryl of 6 to 18 carbons and arylalkyl of 7 to 26 carbons. The monophosphoric acids used according to the invention will form precipitates with the bioactive agent.

Suitable sulfonic organic acids include but are not limited to monosulfonic acids of about 6 to 100 carbons, as well as disulfonic acids, tri phosphoric acids, tetraphosphoric acids and pentaphosphoric acids having from 2 to 100 carbons. These sulfonic organic acids may be saturated, unsaturated, aromatic and linear or branched in carbon structure; and may be unsubstituted by groups other than hydrogen or oxygen, or optionally substituted by such groups as halo, nitro, and the like. Partial sulfonic esters having at least one acidic sulfonic group are also included. The esterifying groups include alkyl of 1 to 10 carbons aryl of 6 to 18 carbons and arylalkyl of 7 to 26 carbons. The monosulfonic acids used according to the invention will form precipitates with the bioactive agent.

In one embodiment of the invention the stabilizing associate is a polyprotic organic acid. The polyprotic organic acid may be selected from citric acid, tartaric acid, malic acid, maleic acid, malonic acid, oxalic acid, succinic acid, sebacic acid, and editic acid.

The concentration of the stabilizing associate in the delivery system can be calculated against the amount of bioactive agent present. Preferably the ratio between the stabilizing associate and the bioactive agent is about 0.1:1 to about 10:1 expressed on a molar basis. More preferably the ratio between the stabilizing associate and the bioactive agent is about 0.5:1 to about 2:1 expressed on a molar basis.

In one embodiment of the invention the stabilizing associate is a polyprotic carboxylic acid. Preferred stabilizing associates are citric acid, itaconic acid, ascorbic acid, malonic acid and succinic acid. An especially preferred stabilizing associate is citric acid. The concentration of citric acid in the delivery system is preferably from about 0.5% by weight to about 15% by weight of the delivery system, and more preferably from about 1% by weight to about 10% by weight of the delivery system. Alternatively, the concentration of citric acid in the delivery system can be determined on a molar basis against the amount of the bioactive agent. Preferably the amount of citric acid in the delivery system can be from about 0.1:1 to about 10:1 on a molar ratio to the amount of bioactive agent in the delivery system; more preferably the molar ratio is from about 0.5:1 to about 2:1. Most preferably, the molar ratio of citric acid to bioactive agent is about 1:1.

A stabilizing associate can be incorporated into the delivery system by first combining it with a bioactive agent prior to the addition to the other components of the delivery system. A preferred method of preparing the delivery system is to first combine a stabilizing associate with a bioactive agent under conditions to assure molecular interaction prior to combination with the other components of the delivery system. A preferred method is to dissolve the bioactive agent in a suitable solvent and then add the stabilizing associate to interact with or form a complex with the bioactive agent, followed by removal of the solvent by evaporation, precipitation or other means.

In one embodiment of the invention, the stabilizing associate is an organic carboxylic acid that is not freely soluble in water. Examples include longer chain fatty acids such as pimelic acid, oleic acid, linoleic acid, linolenic acid, lauric acid, pamoic acid, isostearic acid, palmitic acid and the like. When such a fatty acid is added to an aqueous solution of a bioactive agent, the fatty acid can combine with the bioactive agent to form a water-insoluble salt of the bioactive agent. The precipitated salt can be separated from the aqueous solution, by a suitable means such as filtration or lyophilization. The resulting bioactive agent/stabilizing associate mixture may be prepared as a stable form of the bioactive agent for use in controlled release implants. The mixture can be combined with the other components of the delivery system to form a stable and consistent delivery system for administration and implant formation. In one embodiment of the invention, the stabilizing associate is a fatty acid such as oleic acid and palmoic acid, and the bioactive agent octreotide acetate or GHRP1.

The Biocompatible, Biodegradable, Thermoplastic Polymer

The delivery system includes a biocompatible, biodegradable, thermoplastic polymer that that is substantially insoluble in an aqueous medium. The biocompatible, biodegradable, thermoplastic polymers used according to the invention can be made from a variety of monomers which form polymer chains or monomeric units joined together by their linking groups. These include polymers with polymer chains or backbones containing such linking groups as ester, anhydride and carbonate. These polymers are usually formed by reaction of starting monomers containing the reactant groups that will form these backbone functional groups. For example, diols and dicarboxylic acids; hydroxycarboxylic acids; or lactone dimers and trimers of hydroxycarboxylic acids; i.e., cyclic dimers of hydroxycarboxylic acids and cyclic trimers of hydroxycarboxylic acids, will form polyesters having the ester linking groups. Any aliphatic, aromatic or arylalkyl starting monomer having the specified functional groups can be used according to the invention to make the branched thermoplastic polymers of the invention, provided that the polymers and their degradation products are biocompatible. The monomer or monomers used in forming the thermoplastic polymer may be of a single or multiple identity. The resultant thermoplastic polymer will be a homopolymer formed from one monomer, or one set of monomers when a diol and diacid are used, or a copolymer, terpolymer, or multipolymer formed from two or more, or three or more, or more than three monomers or sets of monomers respectively. The biocompatibility specifications of such starting monomers are known in the art.

Generally, the biodegradable, biocompatible thermoplastic polymer of the delivery system of the present invention may be a linear polymer, or a branched or star polymer, or a mixture of a linear polymer and a branched and/or star polymer. A linear thermoplastic polymer used in the present invention is constructed of difunctional monomeric units so that the polymer chains have no branch points. A branched or star thermoplastic polymer used in the present invention may be at least trifunctional, or may be multifunctional. This multifunctional character provides at least some branching of the resulting polymer chain.

The thermoplastic polymers useful according to the invention are substantially insoluble in aqueous media and body fluids, preferably essentially completely insoluble in such media and fluids. They are also capable of dissolving or dispersing in selected organic solvents having a water solubility ranging from completely soluble in all proportions to water insoluble. They also are biocompatible.

The thermoplastic polymers useful according to the invention may have average molecular weights ranging from about 1 kiloDalton (kD) to about 1,000 kD, preferably from about 2 kD to about 500 kD, more preferably from abut 5 kD to about 200 kD, and most preferably from about 5 kD to about 100 kD. The molecular weight may also be indicated by the inherent viscosity (abbreviated as "I.V.", units are in deciliters/gram). Generally, the inherent viscosity of the thermoplastic polymer is a measure of its molecular weight and degradation time (e.g., a thermoplastic polymer with a high inherent viscosity has a higher molecular weight and longer degradation time). Preferably, the thermoplastic polymer has a molecular weight, as shown by the inherent viscosity, from about 0.05 dL/g to about 2.0 dL/g (as measured in chloroform), more preferably from about 0.10 dL/g to about 1.5 dL/g.

When used in the monolithic material or microparticle embodiments of the invention, the thermoplastic polymer has the physical state of a solid or a shape-retaining gel. These embodiments may be rigid so that they cannot be flexed or bent by squeezing them between a patient's fingers or they may be flexible or bendable so that they can be compressed or flexed out of original shape by squeezing between a patient's fingers (i.e., a low amount of force). The thermoplastic polymer functions as a matrix in these embodiments to provide integrity to the single body solid or gel and to enable controlled release of the bioactive agent upon implantation.

When used in the flowable composition embodiment of the invention, the thermoplastic polymer in combination with the organic solvent provides a viscosity of the flowable composition that varies from low viscosity, similar to that of water, to a high viscosity, similar to that of a paste, depending on the molecular weight and concentration of the thermoplastic polymer. Typically, the polymeric composition includes about 10 wt % to about 80 wt %, more preferably about 30 wt % to about 60 wt % of a thermoplastic polymer.

In a preferred example of the invention, the delivery system includes as a thermoplastic polymer poly(lactide-co-glycolide) polymer (PLG). The thermoplastic polymer has a ratio of from 50/50 to 85/15 lactide to glycolide. This thermoplastic polymer has an inherent viscosity of from about 0.1 dL/g to about 0.4 dL/g. Preferably the concentration of the PLG polymer is from about 10% to about 60% by weight of the delivery system.

Optionally, the delivery system may contain a combination of a non-polymeric material and an amount of a thermoplastic polymer. The combination of non-polymeric material and thermoplastic polymer may be adjusted and designed to provide a more coherent solid implant or a delivery system.

Non-polymeric materials useful in the present invention are those that are biocompatible, substantially insoluble in water and body fluids, and biodegradable and/or bioerodible within the body of an animal. The non-polymeric material is capable of being at least partially solubilized in an organic solvent. In the flowable composition embodiment of the delivery system and the monolithic material and microparticle embodiments containing some organic solvent or other additive, the non-polymeric materials are also capable of coagulating or solidifying to form a solid implant upon the dissipation, dispersement or leaching of the solvent component from the delivery system upon contact of the non-polymeric material with a body fluid. The matrix of all embodiments of the delivery system including a non-polymeric material will have a firm consistency ranging from gelatinous to impressionable and moldable, to a hard, dense solid.

Non-polymeric materials that can be used in the delivery system generally include any having the foregoing characteristics. Examples of useful non-polymeric materials include sterols such as cholesterol, stigmasterol, beta-sistosterol, and estradiol; cholesteryl esters such as cholesteryl stearate, C18-C36 mono-.di-, and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl tridocosanoate, glyceryl trimyristate, glyceryl tridecanoate, glyceryl tristearate and mixtures thereof; sucrose fatty acid esters such as sucrose distearate and sucrose palmitate; sorbitan fatty acid esters such as sorbitan monostearate, sorbitan monopalmitate, and sorbitan tristearate; C16-C18 fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof, sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glyceryl tristearate, stearic acid, stearic anhydride, glyceryl monooleate, glyceryl monolinoleate, and acetylated monoglycerides.

The control of molecular weight and/or inherent viscosity of the thermoplastic polymer is significant toward the formation and performance of the implant. In general, thermoplastic polymers with higher molecular weight and higher inherent viscosity will provide an implant with a slower degradation rate and therefore a longer duration. Changes and fluxuations of the molecular weight of the thermoplastic polymer following the compounding of the delivery system will result in the formation of an implant that shows a degradation rate and duration substantially different from the degradation rate and duration desired or predicted. For the formation of consistent implants it is necessary to maintain a stable range for the molecular weight of the selected thermoplastic polymers within the delivery system. As discussed above, a nucleophilic attack of the bioactive agent upon the thermoplastic polymer will affect the molecular weight of the thermoplastic polymer.

The polymeric and non-polymeric materials may be selected and/or combined to control the rate of biodegradation, bioerosion and/or bioabsorption within the implant site. Generally, the implant matrix will breakdown over a period from about 1 week to about 12 months, preferably over a period of about 1 week to about 4 months.

Organic Liquid

Organic liquids suitable for optional use in the monolithic material and microparticle embodiments of the delivery system and for use in the flowable composition embodiment of the delivery system are biocompatible and display a range of solubilities in aqueous medium, body fluid, or water. That range includes complete insolubility at all concentrations upon initial contact, to complete solubility at all concentrations upon initial contact between the organic liquid and the aqueous medium, body fluid or water.

While the solubility or insolubility of the organic liquid in water can be used as a solubility guide according to the invention, the water solubility or insolubility typically will vary from the solubility or insolubility in an aqueous medium and especially in body fluid. Relative to water, an aqueous medium containing physiologic salts, lipid, proteins and the like will have a differing solvating ability for organic liquids. It may be higher or lower than that of water as exemplified by the classic "salting out" procedure. Body fluid displays similar variability relative to water but in contrast to a "salting out" factor, body fluid typically has a higher solvating ability for most organic liquids than does water. This higher ability is due in part to the greater lipophilic character of body fluid relative to water, and also in part to the dynamic character of body fluid. In a living organism, body fluid is not static but rather moves throughout the organism. In addition, body fluid is purged or cleansed by tissues of the organism so that body fluid contents are removed. As a result, body fluid in living tissue will remove, solvate or dissipate organic liquids that are utterly insoluble in water.

Pursuant to the foregoing understanding of the solubility differences among water, aqueous media and body fluid, the organic liquid used in the present invention may be completely insoluble to completely soluble in water when the two are initially combined. Preferably the organic liquid is at least slightly soluble, more preferably moderately soluble, especially more preferably highly soluble, and most preferably soluble at all concentrations in water. The corresponding solubilities of the organic liquids in aqueous media and body fluid will tend to track the trends indicated by the water solubilities. In body fluid, the solubilities of the organic liquids will tend to be higher than those in water.

When an organic liquid that is insoluble to only slightly soluble in body fluid is used in any of the embodiments of the delivery system, it will allow water to permeate into the implanted delivery system over a period of time ranging from seconds to weeks or months. This process may negatively or positively affect the delivery rate of the bioactive agent and in the case of the flowable composition, it will affect the rate of coagulation or solidification. When an organic liquid that is moderately soluble to very soluble in body fluid is used in any of the embodiments of the delivery system, it will diffuse into body fluid over a period of minutes to days. The diffusion rate may negatively or positively affect the delivery rate of the bioactive agent. When highly soluble organic liquids are used, they will diffuse from the delivery system over a period of seconds to hours. Under some circumstances, this rapid diffusion is responsible at least in part for the so-called burst effect. The burst effect is a short-lived but rapid release of bioactive agent upon implantation of the delivery system followed by a long-lived slow release of bioactive agent.

The organic liquids used in the delivery system of the present invention also have an effect upon the rate of hydrolysis of the polymer by the nucleophilic bioactive agent. With the nucleophilic bioactive agent being kept the same, a highly water soluble solvent such as NMP will promote a relatively rapid degradation of the polymer while a slightly water soluble solvent such as ethyl acetate will permit a relatively slow degradation of the polymer. This rate of degradation is also tempered by the strength of the nucleophilic bioactive agent.

Organic liquids used in the delivery system of the present invention include aliphatic, aryl, and arylalkyl; linear, cyclic and branched organic compounds that are liquid or at least flowable at ambient and physiological temperature and contain such functional groups as alcohols, alkoxylated alcohols, ketones, ethers, polymeric ethers, amides, esters, carbonates, sulfoxides, sulfones, any other functional group that is compatible with living tissue, and any combination thereof. The organic liquid preferably is a polar aprotic or polar protic organic solvent. Preferably, the organic liquid has a molecular weight in the range of about 30 to about 1000.

Preferred biocompatible organic liquids that are at least slightly soluble in aqueous or body fluid include N-methyl-2-pyrrolidone, 2-pyrrolidone; $C_1$ to $C_{15}$ alcohols, diols, triols and tetraols such as ethanol, glycerine, propylene glycol, butanol; $C_3$ to $C_{15}$ alkyl ketones such as acetone, diethyl ketone and methyl ethyl ketone; $C_3$ to $C_{15}$ esters and alkyl esters of mono-, di-, and tricarboxylic acids such as 2-ethoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; $C_1$ to $C_{15}$ amides such as dimethylformamide, dimethylacetamide and caprolactam; $C_3$ to $C_{20}$ ethers such as tetrahydrofuran, or solketal; tweens, triacetin, decylmethylsulfoxide, dimethyl sulfoxide, oleic acid, and 1-dodecylazacycloheptan-2-one as 5-hydroxy N-methyl-2-pyrrolidone, esters of carbonic acid and alkyl alcohols such as propylene carbonate, ethylene carbonate, and dimethyl carbonate; alkyl ketones such as acetone and methyl ethyl ketone; alcohols such as solketal, glycerol formal, and glycofurol; dialkylamides such as dimethylformamide, dimethylacetamide, dimethylsulfoxide, and dimethylsulfone; lactones such as epsilon-caprolactone and butyrolactone; cyclic alkyl amides such as caprolactam; triacetin and diacetin; aromatic amides such as N,N-dimethyl-m-toluamide, and 1-dodecylazacycloheptan-2-one; and mixtures and combinations thereof. Preferred solvents include N-methyl-2-pyrrolidone, 2-pyrrolidone, dimethylsulfoxide, ethyl lactate, propylene carbonate, solketal, glycerol formal, isopropylidene glycol, and glycofurol.

Other preferred organic liquids are benzyl alcohol, benzyl benzoate, dipropylene glycol, tributyrin, ethyl oleate, glycerin, glycofurol, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of their solvating ability and their compatibility.

The type and amount of biocompatible organic liquid present in the delivery system will typically depend on the desired properties of the controlled release implant as described in detail below. Preferably, the delivery system includes about 0.001 wt % to about 90 wt %, more preferably about 5 wt % to about 70 wt %, most preferably 5 to 50 wt % of an organic liquid. Generally, the monolithic material and microparticle embodiments optionally include organic liquid. When present, its concentration can range from 0.001 wt % to 30 wt % relative to the total weight. Generally the flowable composition embodiment includes organic liquid in the range of 1 wt % to 90 wt % relative to the total weight of the composition.

The solubility of the biodegradable thermoplastic polymers in the various organic liquids will differ depending upon their crystallinity, their hydrophilicity, hydrogen-bonding, and molecular weight. Lower molecular-weight polymers will normally dissolve more readily in the organic liquids than high-molecular-weight polymers. As a result, the concentration of a polymer dissolved in the various organic liquids will differ depending upon type of polymer and its molecular weight. Moreover, the higher molecular-weight polymers will tend to give higher solution viscosities than the low-molecular-weight materials.

When the organic liquid forms part of the flowable composition embodiment of the invention, it functions not only to enable easy, non-surgical placement of the delivery system into living tissue, it also facilitates transformation of the flowable composition to an in situ formed implant. Although it is not meant as a limitation of the invention, it is believed that the transformation of the flowable composition is the result of the dissipation of the organic liquid from the flowable composition into the surrounding body fluid and tissue and the infusion of body fluid from the surrounding tissue into the flowable composition. It is believed that during this transformation, the thermoplastic polymer and organic liquid within the flowable composition partition into regions rich and poor in polymer.

For the flowable composition of the invention only, the concentration of the thermoplastic polymer in the organic liquid according to the invention will range from about 0.01 g per ml of organic liquid to a saturated concentration. Typically, the saturated concentration will be in the range of 80 to 95 wt % solids or 4 to almost 5 gm per ml of organic liquid, assuming that the solvent weighs approximately 1 gm per ml.

For polymers that tend to coagulate slowly, a solvent mixture can be used to increase the coagulation rate. In essence, one liquid component of the solvent mixture is a good solvent for the polymer, and the other liquid component of the solvent mixture is a poorer solvent or a non-solvent. The two liquids are mixed at a ratio such that the polymer is still soluble but precipitates with the slightest increase in the amount of non-solvent, such as water in a physiological environment. By necessity, the solvent system must be miscible with both the polymer and water. An example of such a binary solvent system is the use of N-methylpyrrolidone and ethanol. The addition of ethanol to the NMP/polymer solution increases its coagulation rate.

For the monolithic and microparticle embodiments of the invention, the presence of the organic liquid can serve to provide the following properties: plasticization, moldability, flexibility, increased or decreased homogeneity, increased or decreased release rate for the bioactive agent, leaching, promotion or retardation of body fluid influx into the implant, patient comfort, compatibility of thermoplastic polymer and bioactive agent and the like. Generally the concentration of organic liquid in the monolithic material or microparticles may range from about 0.001 wt. percent to as much as about 30 wt. percent. Generally, the concentration will be less than an amount that would cause conversion of the monolithic material or microparticles into a flowable composition. Also the organic liquid may preferentially be chosen so as to display less than substantial ability to dissolve the thermoplastic polymer.

The pliability of the implanted delivery system can be substantially maintained throughout its life if additives such as the organic liquid are maintained in the implanted system. Such additives also can act as a plasticizer for the thermoplastic polymer and at least in part may remain in the implanted delivery system. One such additive having these properties is an organic liquid of low water solubility to water insolubility. Such an organic liquid providing these pliability and plasticizing properties may be included in the delivery system as the sole organic liquid or may be included in addition to an organic liquid that is moderately to highly water soluble.

Organic liquids of low water solubility or water insolubility, such as those forming aqueous solutions of no more than 5% by weight in water, can function as a pliability plasticizing component and in addition can act as the solvating component for the flowable composition embodiment of the invention. Such organic liquids can act as plasticizers for the thermoplastic polymer. When the organic liquid has these properties, it is a member of a subgroup of organic solvents termed "plasticizer organic liquids" herein. The plasticizer organic liquid influences the pliability and moldability of the implant composition such that it is rendered more comfortable to the patient when implanted. Moreover, the plasticizer organic liquid has an effect upon the rate of sustained release of the biologically active agent such that the rate can be increased or decreased according to the character of the plasticizer organic liquid incorporated into the implant composition. In general, the organic liquid acting as a plasticizer is believed to facilitate molecular movement within the solid thermoplastic matrix. The plasticizing capability enables polymer molecules of the matrix to move relative to each other so that pliability and easy moldability are provided. The plasticizing capability also enables easy movement of the bioactive agent so that in some situations, the rate of sustained release is either positively or negatively affected.

High Water Solubility Organic Liquids

A moderate to highly water soluble organic liquid can be generally used in the flowable composition embodiment of the invention, especially when pliability will not be an issue after implantation of the implant composition. Use of the highly water soluble organic liquid will provide an implant having the physical characteristics of and implant made through direct insertion of the flowable composition. Such implants and the precursor flowable compositions are described, for example in U.S. Pat. Nos. 4,938,763 and 5,278,201, the disclosures of which are incorporated herein by reference.

Use of a moderate to highly water soluble organic liquid in the monolithic material and microparticle embodiments of the invention will facilitate intimate combination of the other components. It will promote solid or gel homogeneity and pliability of the embodiments so that they can be readily inserted into appropriate incisions or trocar placements in tissue.

Useful, highly water soluble organic liquids include, for example, substituted heterocyclic compounds such as N-methyl-2-pyrrolidone (NMP) and 2-pyrrolidone; $C_2$ to $C_{10}$ alkanoic acids such as acetic acid and lactic acid, esters of hydroxy acids such as methyl lactate, ethyl lactate, alkyl citrate and the like; monoesters of polycarboxylic acids such as monomethyl succinate acid, monomethyl citric acid and the like; ether alcohols such as glycofurol, glycerol formal, isopropylidene glycol, 2,2-dimethyl-1,3-dioxolane-4-methanol; Solketal; dialkylamides such as dimethylformamide, dimethylacetamide; dimethylsulfoxide (DMSO) and dimethylsulfone; lactones such as epsilon, caprolactone and butyrolactone; cyclic alkyl amides such as caprolactam; and mixtures and combinations thereof. Preferred organic liquids include N-methyl-2-pyrrolidone, 2-pyrrolidone, dimethylsulfoxide, ethyl lactate, glycofurol, glycerol formal, and isopropylidene glycol.

Low Water Solubility Organic Liquids/Solvents

As described above, an organic liquid of low or no water solubility (hereinafter a lono liquid) may also be used in the delivery system. Preferably, a lono liquid is used when it is desirable to have an implant that remains pliable, is to be extrudable is to have an extended release and the like. For example, the release rate of the biologically active agent can be affected under some circumstances through the use of a lono liquid. Typically such circumstances involve retention of the organic liquid within the implant product and its function as a plasticizer.

Examples of lono liquids include esters of carbonic acid and aryl alcohols such as benzyl benzoate; $C_4$ to $C_{10}$ alkyl alcohols; $C_1$ to $C_6$ alkyl $C_2$ to $C_6$ alkanoates; esters of carbonic acid and alkyl alcohols such as propylene carbonate, ethylene carbonate and dimethyl carbonate, alkyl esters of mono-, di-, and tricarboxylic acids, such as 2-ethoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as methyl ethyl ketone; as well as other carbonyl, ether, carboxylic ester, amide and hydroxy containing liquid organic compounds having some solubility in water. Propylene carbonate, ethyl acetate, triethyl citrate, isopropyl myristate, and glyceryl triacetate are preferred because of biocompatibility and pharmaceutical acceptance.

Additionally, mixtures of the foregoing high and lono liquids providing varying degrees of solubility for the matrix forming material can be used to alter the life time, rate of bioactive agent release and other characteristics of the implant. Examples include a combination of N-methylpyrrolidone and propylene carbonate, which provides a more hydrophobic solvent than N-methyl pyrrolidone alone, and a combination of N-methylpyrrolidone and polyethylene glycol, which provides a more hydrophilic solvent than N-methylpyrrolidone alone.

The organic solvent for inclusion in the composition should be biocompatible. Biocompatible means that the organic solvent as it disperses or diffuses from the composition does not result in substantial tissue irritation or necrosis surrounding the implant site.

Other Additives

The delivery system may optionally include polymeric controlled release additives such as rate release retarding agents, rate release acceleration agents, pore forming agents, plasticizers, encapsulation agents for encapsulating the bioactive agent, thermal gelling agents, burst effect reducing materials, hydrogels, polyhydroxyl materials, leaching agents, tissue transporting agents (i.e., penetration enhancers), solubilization agents and other similar additives.

Optionally the delivery system may include a polymeric controlled release additive. The presence of a polymeric controlled release additive in the delivery system substantially reduces the "initial burst" of active agent released from the delivery system during the initial stage of implantation.

According to the invention, the controlled release additive may be thermoplastic polymer having polyester moieties and polyether or polyol moieties. Preferably the polyester is a lactide, glycolide, caprolactone polymer containing one or any combination of these monomers. Preferably the polyether or polyol is polyethylene glycol, polypropylene glycol, polybutylene glycol and the like. Especially preferably, the additive is a PLG/PEG block copolymer. Examples include a PLG/PEG block polymer which includes from about 50 mole % to about 90 mole % lactide monomers and about 50 mole % to about 10 mole % glycolide monomers. More preferably, the PLG/PEG block polymer includes from about 50 mole % to about 75 mole % lactide monomers and about 50 mole % to about 25 mole % glycolide monomers. Preferably the PEG moiety has a molecular weight of about 1,000 Daltons to about 10,000 Daltons, more preferably about 5,000 Daltons.

The PEG portion of the block copolymer ranges from about 1 wt % to about 20 wt % of the total weight of the block copolymer. The percentage is dependent on the molecular weight of the block copolymer that is prepared and the molecular weight of the polyethylene glycol that is used.

The inherent viscosity (abbreviated as "I.V."; units are in deciliters/gram) of the polymeric controlled release additive is a measure of its molecular weight. Preferably, the inherent viscosity of the controlled release additive is from about 0.50 dL/g to about 1.0 dL/g (as measured in chloroform), more preferably from about 0.70 dL/g to about 0.90 dL/g.

Examples of suitable polymeric controlled release additives include 50/50 PLG/PEG-5000 (0.81 dL/g); 70/30 PLG/PEG-5000 (0.73 dL/g); and 70/30 PLG/PEG-5000 (0.79 dL/g).

The polymeric controlled release additive is present in the polymeric delivery system in an amount effective to reduce the initial burst of active agent from the delivery system during the first 24 hours after implantation. Preferably, the delivery system includes about 1 wt % to about 50 wt %, more preferably about 2 wt % to about 20 wt % of the polymeric controlled release additive.

Release Rate Modification Agent

Rate modifying agents, plasticizers and leachable agents can be included to manage the rate of release of bioactive agent and the pliability of the matrix. Known plasticizers as well as organic compounds that are suitable for secondary pseudobonding in polymer systems are acceptable as pliability modifiers and leaching agents. Generally these agents are esters of mono, di and tricarboxylic acids, diols and polyols, polyethers, non-ionic surfactants, fatty acids, fatty acid esters, oils such as vegetable oils, and the like. The concentrations of such agents within the solid matrix can range in amount up to 60 wt % relative to the total weight of the matrix, preferably up to 30 wt % and more preferably up to 15 wt %. Generally, these leaching agents, plasticizers and pliability modifiers and their application are described in U.S. Pat. Nos. 5,702,716 and 5,447,725, the disclosures of which are incorporated herein by reference with the proviso that the polymers to be used are the biocompatible, biodegradable, thermoplastic polymers of the present invention.

A release rate modification agent may also be included in the delivery system for controlling the rate of breakdown of the implant matrix and/or the rate of release of a bioactive agent in vivo from the implant matrix. The rate modifying agent can increase or retard the rate of release depending upon the nature of the rate modifying agent incorporated into the solid matrix according to the invention. Examples of suitable substances for inclusion as a release rate modification agent include dimethyl citrate, triethyl citrate, ethyl-heptanoate, glycerin, hexanediol, and the like.

The delivery system may include a release rate modification agent to provide controlled, sustained release of a bioactive agent from the implant matrix. Although not intended to be a limitation to the present disclosure, it is believed the release rate modification agent alters the release rate of a bioactive agent from the implant matrix by changing the hydrophobicity of the polymer implant.

The use of a release rate modification agent may either decrease or increase the release of the bioactive agent in the range of multiple orders of magnitude (e.g., 1 to 10 to 100), preferably up to a ten-fold change, as compared to the release of a bioactive agent from a solid matrix without the release rate modification agent. Release rate modification agents which are hydrophilic, such as polyethylene glycol, may increase the release of the bioactive agent. By an appropriate choice of the polymer molecular weight in combination with an effective amount of the release rate modification agent, the release rate and extent of release of a bioactive agent from the implant matrix may be varied, for example, from relatively fast to relatively slow.

Useful release rate modification agents include, for example, organic substances which are water-soluble, water-miscible, or water insoluble (i.e., water immiscible), with water-insoluble substances preferred.

The release rate modification agent is preferably an organic compound which will substitute as the complementary molecule for secondary valence bonding between polymer molecules, and increases the flexibility and ability of the polymer molecules to slide past each other. Such an organic compound preferably includes a hydrophobic and a hydrophilic region so as to effect secondary valence bonding. It is preferred that a release rate modification agent is compatible with the combination of polymers and solvent used to formulate polymer solution. It is further preferred that the release rate modification agent is a pharmaceutically-acceptable substance.

Useful release rate modification agents include, for example, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebacate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; vegetable oils obtained from seeds, flowers, fruits, leaves, or stem of a plant or tree, such as sesame oil, soybean oil, cotton seed oil, almond oil, sunflower oil, and peanut oil; sterols, such as cholesterol; alcohols, such as $C_6$-$C_{12}$ alkanols, 2-ethoxyethanol, and the like. The release rate modification agent may be used singly or in combination with other such agents. Suitable combinations of release rate modification agents include, for example, glycerin/propylene glycol, sorbitol/glycerine, ethylene oxide/propylene oxide, butylene glycol/adipic acid, and the like. Preferred release rate modification agents include dimethyl citrate, triethyl citrate, ethyl heptanoate, glycerin, and hexanediol.

The amount of the release rate modification agent included in the delivery system will vary according to the desired rate of release of the bioactive agent from the implant matrix. Preferably, the delivery system contains about 0.5-15%, preferably about 5-10%, of a release rate modification agent.

Pore Forming Agent/Additive

Additives can be used to advantage in further controlling the pore size in the solid matrix, which influences the structure of the matrix and the release rate of a bioactive agent or the diffusion rate of body fluids. For example, if the delivery system is too impervious to aqueous medium, water or tissue ingrowth so that no or little bioactive agent is released, a pore-forming agent can be added to generate additional pores in the matrix. Any biocompatible water-soluble material can be used as the pore-forming additive. These additives can be either soluble in the delivery system or simply dispersed within it. They are capable of dissolving, diffusing or dispersing out of both the implanted polymer matrix whereupon pores and microporous channels are generated. The amount of pore-forming additive (and size of dispersed particles of such pore-forming agent, if appropriate) within the delivery system will directly affect the size and number of the pores in the polymer matrix.

Pore-forming additives include any pharmaceutically acceptable organic or inorganic substance that is substantially miscible in water and body fluids and will dissipate from the implanted polymeric matrix into aqueous medium or body fluids or water-immiscible substances that rapidly degrade to water soluble substances. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming additive incorporated into the flowable composition.

The pore-forming additive may dissipate from the matrix into the surrounding tissue fluids at a rate slower than that of the organic liquid if one is present, or be released from the matrix over time by biodegradation or bioerosion of the matrix. Preferably, the pore-forming additive dissipates from the implant matrix within a short time following implantation such that a matrix is formed with a porosity and pore structure effective to perform the particular purpose of the implant, as for example, a barrier system for a tissue regeneration site, a matrix for timed-release of a drug or medicament, and the like.

The concentration of the pore-forming agent relative to polymer in the composition may be varied to achieve different degrees of pore-formation, or porosity, in the matrix. Generally, the delivery system may include about 0.01-1 gram of pore-forming agent per gram polymer.

The size or diameter of the pores formed in the matrix of the implant may be modified according to the size and/or distribution of the pore-forming agent within the polymer matrix. For example, pore-forming agents that are relatively insoluble in the polymer mixture may be selectively included in the delivery system according to particle size in order to generate pores having a diameter that corresponds to the size of the pore-forming agent. Pore-forming agents that are soluble in the polymer mixture may be used to vary the pore size and porosity of the implant matrix by the pattern of distribution and/or aggregation of the pore-forming agent within the polymer matrix.

Pore diameter and distribution within the polymer matrix of the implant may be measured, as for example, according to scanning electron microscopy methods by examination of cross-sections of the polymer matrix. Porosity of the polymer matrix may be measured according to suitable methods known in the art, as for example, mercury intrusion porosimetry, specific gravity or density comparisons, calculation from scanning electron microscopy photographs, and the like. Additionally, porosity may be calculated according to the proportion or percent of water-soluble material included in the polymer composition. For example, a flowable composition which contains about 30% polymer and about 70% solvent and/or other water-soluble components will generate an implant having a polymer matrix of about 70% porosity. A monolithic material which contains about 30% pore forming additive with generate an implant having a polymer matrix of about 20 to 25% porosity.

The delivery system of the invention is designed for implantation into the body of a mammal. It is particularly important that such a delivery system result in minimal tissue irritation when implanted or injected into vasculated tissue. As a structural medical device, the delivery system of the invention provides a physical form having specific chemical, physical, and mechanical properties sufficient for the application and a polymer matrix that degrades in vivo into non-toxic residues.

The implant formed by placement of the delivery system will slowly biodegrade within the body and allow natural tissue to grow and replace the impact as it disappears. The implant formed will release the drug contained within its matrix at a controlled rate until the drug is depleted. With certain drugs, the polymer will degrade after the drug has been completely released. With other drugs such as peptides or proteins, the drug will be completely released only after the polymer has degraded to a point where the non-diffusing drug has been exposed to the body fluids.

Biodegradable, Crystallization-Controlling Agent

A crystallization-controlling agent may optionally be combined with the polymer to effect homogeneity of the polymer mass, that is, a substantially uniform distribution of crystalline sections of the polymer to achieve a homogeneous mass having the desired physical characteristics of moldability, cohesion, and stability for effective use with bone and other tissues. The crystallization-controlling agent may be in the form of a dispersed solid particle in the delivery system, for example, an inorganic salt such as calcium carbonate or calcium phosphate, a polymer such as poly(vinyl alcohol), starch or dextran, and other like substance. Other useful crystallization-controlling agent are those substances that are either melted with the polymer during the compounding process, or soluble in the molten polymer. Examples of those substances include low molecular weight organic compounds such as glycerol palmitate or ethyl lactate, polymers such as poly(ethylene glycol) or poly(lactide-co-caprolactone), and other like substances. Compositions formulated with a crystallization-controlling agent include about 40-95 wt-% of the polymer, preferably about 60-90 wt-%, and about 5-60 wt-% of the crystallization-controlling agent, preferably about 10-40 wt-%.

Crystallization-controlling agents suitable for use in the present compositions may be divided into two major classes, those that persist in the form of a solid particulate in the molten composition, and those that melt or dissolve in the molten polymer composition.

Crystallization-controlling agents that will persist as solid particles, or fillers, in the composition include inorganic or organic salts, and polymers. Suitable inorganic salts include, for example, calcium carbonate, hydroxy appetite, calcium phosphate, calcium appetite, calcium sulfate, calcium bicarbonate, calcium chloride, sodium carbonate, sodium bicarbonate, sodium chloride, and other like salts. Suitable organic salts include for example, calcium stearate, calcium palmitate, sodium stearate, other metallic salts of $C_{10}$-$C_{50}$ fatty acid derivatives, and other like salts. Polymers suitable for use in the composition that persist as dispersed particles or fillers in the composition include, for example, polysaccharides, cellulose derivatives and poly(vinyl alcohol). Examples of suitable polysaccharides include, for example, dextran, maltodextrin, starches derived from corn, wheat, rice and the like, and starch derivatives such as sodium starch glycolate. Examples of suitable cellulose derivatives include for example, sodium carboxymethyl cellulose, crosslinked sodium carboxymethyl cellulose, carboxylmethyl cellulose, hydroxyethyl cellulose, and the like. Suitable poly(vinyl alcohol)s have a molecular weight of about 5,000 to 20,000, preferably about 10,000-15,000, with a percent hydrolysis of about 80-100%.

Crystallization-controlling agents which either melt with or dissolve into the molten polymer during compounding may also be used in the polymer compositions of the invention. These compositions may or may not undergo some degree of phase separation during cooling. Crystallization-controlling agents of this type include low molecular weight organic compounds and polymers. Suitable low molecular weight compounds include, for example, glycerol, palmitate, glycerol stearate and other like glycerol derivatives, triethyl citrate and other like citric acid derivatives, ethyl lactate and other like esters, and the like.

The crystallization-controlling agent is included in the delivery system in an amount effective to soften the polymer to a moldable and/or smearable consistency. Preferably, the crystallization-controlling agent is a non-solvent, solid substance. A crystallization-controlling agent may be included in the composition alone or in combination with another crystallization-controlling agent. An example of a preferred combination of such agents is poly(lactide-co-caprolactone) and calcium stearate.

Penetration Enhancer

The delivery system may further comprise a penetration enhancer effective to improve the penetration of the biological agent into and through bodily tissue, with respect to a system lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol. The penetration enhancer can be present in the flowable composition in any suitable and appropriate amount (e.g., between about 1 wt. % and about 10 wt. %)

Solubilization Agent

A solubilization agent for promoting a dispersion or solution of the bioactive agent-stabilizing associate complex in solvent or organic liquid can be employed in the present invention. The solubilization agent can function as a surfactant or emulsifying agent or as iconicity modifying agent. Such materials include nonionic surfactants, soaps, weakly ionizing cationic or anionic surfactants, inorganic salts, and mild acids. The concentration of the solubilizing agent may be significantly less than a stoichiometric molar amount relative to the bioactive agent-stabilizing associate complex. Examples include tweens surfactants, polyethylene oxide, amphoteric surfactants, sodium chloride, sodium palmitate, sodium stearate, sodium acetate and acetic acid.

Absorption Altering Agent

Any suitable and appropriate absorption altering agent can be employed in the present invention. For example, the absorption altering agent can be selected from the group of propylene glycol, glycerol, urea, diethyl sebacate sodium, lauryl sulfate, sodium lauryl sulfate, sorbitan ethoxylates, oleic acid, pyrrolidone carboxylate esters, N-methylpyrrolidone, N,N-diethyl-m-tolumide, dimethyl sulfoxide, alkyl methyl sulfoxides, and combinations thereof.

Opacification Agent

Any suitable and appropriate opacification agent can be employed in the present invention. For example, the opacification agent can be selected from the group of barium, iodine, calcium, and any combination thereof.

Colorant

Colorants can also be added to the delivery system in an amount effective to allow monitoring of the biodegradability or bioerodibility of the implanted system over time. Suitable and appropriate colorants will be nontoxic, non-initiating and non-reactive with the other components of the delivery system. Colorants which have been approved by the FDA for use in cosmetics, foods and drugs include: D & C Yellow No. 7; D & C Red No. 17; D & C Red No. 7, 9, and 34; FD & C Red No. 4; Orange D & C No. 4; FD & C Blue 2; FD & C Green No. 3, and the like.

Moldable Implant Precursor

A moldable implant can be formed by combination of a flowable composition and a small amount an aqueous medium such as water or saline, or contact with a body fluid such as blood serum, lymph, and the like pursuant to the techniques disclosed in U.S. Pat. No. 5,487,897, the disclosure of which is incorporated herein by reference with the specification that the thermoplastic polymer of the '897 patent is a biocompatible, biodegradable, thermoplastic polymer as described herein.

Briefly, the technique disclosed by the '897 patent converts the flowable composition with or without bioactive agent into a two-part structure comprising an outer sac with a flowable content. The technique applies a limited amount of aqueous medium and the like to a quantity of the pharmaceutical system so that only the outer surface of the system is converted to solid, thus forming the sac with a flowable content inside. The flowable content of the implant precursor may range in consistency from watery to viscous. The outer sac may range in consistency from gelatinous to an impressionable, moldable and waxen-like. The resulting device, or implant precursor, may then be applied to an implant site. Upon implantation, the solvent from the implant precursor diffuses into the surrounding tissue fluids to form an implant having a solid polymer matrix. Preferably, the implant precursor solidifies in situ to a solid matrix within about 0.5-4 hours after implantation, preferably within about 1-3 hours, preferably within about 2 hours. Thus, when placed into an implant site in a body, the implant precursor eventually coagulates to a solid, microporous matrix structure.

MacroStructure

The macrostructure of the solid matrices, e.g., in situ formed implants, monolithic materials, microparticles, implantable articles, biodegradable articles and devices of the invention, is influenced by manner in which they are formed and by the character of the components present in the implanted polymeric matrix. Monolithic materials that are solids or gels and are cast in molds or other similar methods of preparation will generally be nonporous. Microparticles that are formed by evaporative processes such as spray drying or oil/water/oil precipitation will generally be porous. Implants formed from the flowable composition will generally be porous. The porous structure is believed to be formed by several mechanisms and their combinations. The dissipation, disbursement or diffusion of optional organic liquid and pore forming agent out of the polymeric matrix into the adjacent fluids may generate pores, including pore channels, within the polymer matrix. The infusion of aqueous medium, water or body fluid into the polymeric matrix also occurs and is in part also responsible for creation of pores.

Typically, the macroscopic structure of the solid matrix of microparticles or in situ implants formed from a flowable composition involves either a substantially uniform porous structure or a porous core and a porous skin. The size of the pores of the implant, article, device and the like are in the range of about 4-1000 microns, preferably the size of pores of the skin layer are about 1-500 microns. The porosity of such matrices is described by U.S. Pat. No. 5,324,519, the disclosure of which is incorporated herein by reference.

For polymeric matrices formed from a flowable composition according to the invention, it is believed that the porous structure is formed during the transformation of the flowable composition to an implant. During this process, it is believed, as explained above, that the organic solvent and thermoplastic polymer partition within the flowable composition into regions that are rich and poor in thermoplastic polymer. The partition is believed to occur as a result of the dynamic interaction of aqueous infusion and solvent dissipation. The infusion involves movement of aqueous medium, water or body fluid into the flowable composition and the dissipation involves movement of the organic solvent into the medium surrounding the flowable composition. The regions of the flowable composition that are poor in thermoplastic polymer become infused with a mixture of organic solvent and water, aqueous medium or body fluid. These regions are believed to eventually become the porous network of the implant, article and the like.

The Delivery System

The delivery system of the invention is composed of a pharmaceutically acceptable, biodegradable, thermoplastic polymer, an optional pharmaceutically acceptable organic liquid, a stabilizing additive, a bioactive agent containing a nucleophilic functional group, and optionally additives such as a polymeric controlled release additive.

The delivery system of the invention provides a polymeric matrix for the controlled and sustained release of the bioactive agent when implanted. The controlled release can be sustained for a desired period dependent upon the make-up of the delivery system. The period of sustained release can vary from a few days up to a period of several months. With the selections of thermoplastic polymer and other components, the period of sustained release can be controlled to regular application intervals, such as two weeks or 1, 3, or 6 months.

In a preferred method of preparing and administering the delivery system, the bioactive agent is dissolved in a suitable liquid medium. A stabilizing associate is added to the solution. The stabilizing associate may be soluble in the liquid medium. The resulting solution or mixture is then treated to separate a physically stable mixture or complex of the bioactive agent and the stabilizing associate. The mixture or complex of the bioactive agent and the stabilizing associate may be separated from the liquid medium by a suitable means such as filtration or lyophilization.

In a preferred method of preparation the bioactive agent/stabilizing associate mixture is formed by lyophilization. The lyophilized material may be combined with the thermoplastic polymer and optional organic liquid and other option additives as a single formulation suitable for reasonable shelf storage.

Biodegradable drug delivery products can be prepared by any of a number of methods including casting or molding, oil/water/oil coagulation, spray drying, evaporating, film casting, precipitation and transformation. Transformation is the process using water or an aqueous medium or body fluid to cause solidification. Generally, these products are ex vivo solid matrices. If the ex vivo solid matrix is to have a particular shape, it can be obtained by placing the suitable components in a suitable mold and following the implant formation techniques known in the art. Alternatively, the components can be mixed and the mixture can be placed in a closed mold which is contacted with an aqueous medium or is vacuum dried and the like.

Microcapsules and microparticles can be formed by techniques known in the art. Briefly, the microcapsule preparation involves formation of an emulsion of bioactive agent-carrier micelles in a carrier where the carrier is a nonsolvent for the biocompatible, biodegradable, branched thermoplastic polymer of the invention. The micelles are filtered and then suspended in an aqueous medium. The coating of thermoplastic polymer on the surfaces of the micelles then solidifies to form the porous microcapsules. Microparticles are formed in a similar process. A mixture of components including the bioactive agent, thermoplastic polymer, organic liquid and stabilizing associate are added dropwise by spraying, dripping, aerosolizing or by other similar techniques to a nonsolvent for the flowable composition. The size and shape of the droplets is controlled to produce the desired shape and size of the porous microparticles. Sheets, membranes, films, rods, cones and pill shaped monolithic materials can be produced by casting the components with or without optional organic liquid onto a mold or surface of appropriate shape that is coated with a suitable nonsolvent and allowing the monolithic material to solidify. Similarly, the viscosity of the flowable composition can be adjusted so that when sprayed or aerosolized, strings rather than droplets are formed. These strings can be cast upon a nonsolvent for the flowable composition such that a filamentous scaffold or membrane is produced. Also, suture material or other similar material can be formed by extrusion of the flowable composition into a non-solvent bath. The extrusion orifice will control the size and shape of the extruded product. The techniques for formation of these ex vivo solid matrices are described in U.S. Pat. Nos. 4,652,441; 4,917,893; 4,954,298; 5,061,492; 5,330,767; 5,476,663; 5,575,987; 5,480,656; 5,643,607; 5,631,020; 5,631,021; 5,651,990, the disclosures of which are incorporated herein by reference with the proviso that the polymers used are the biocompatible, biodegradable, thermoplastic polymers disclosed herein.

These ex vivo solid matrices can be used according to their known functions. Additionally, the implants and other solid articles are can be inserted in a body using techniques known to the art such as through an incision or by trocar.

The present invention also provides an implant. The implant includes a biodegradable, biocompatible thermoplastic polymer that is at least substantially insoluble in aqueous medium, water or body fluid; and a bioactive agent and a stabilizing associate. The implant has polymeric matrix that may be porous or nonporous. The implant can have any suitable shape and can have any suitable form. For example, the implant can be a solid, semi-solid, wax-like, viscous, or the implant can be gelatinous.

The implant may be prepared by first combining a bioactive agent with a stabilizing associate to form a mixture. This mixture may be physically and chemically stable for long-term storage. The mixture is combined with the remaining components of the delivery system to form the complete delivery system for packaging and storage, or may be combined just prior to administration to an implant site.

In a preferred preparation for the flowable composition, both the lyophilized material and the thermoplastic polymer/organic solvent base are packaged in syringes. The contents of the syringes can be combined be coupling the syringes and expelling the contents alternately between the syringes. A needle can then be attached to the final syringe filled and the completed delivery system can be injected into one or more sites within a body.

In a preferred embodiment of the invention the bioactive agent is octreotide acetate and the stabilizing associate is citric acid. The two ingredients may be combined by first dissolving them together in purified water and then lyophilizing the resulting solution. The resulting mixture can be combined with the thermoplastic polymer/organic solvent delivery system almost immediately prior to administration to a subject.

In one embodiment the thermoplastic polymer is poly(lactide-co-glycolide) polymer (PLG or PLGH). PLGH is formed from the PLG by the addition of an acid end group on the polymer. Preferably, the organic solvent is n-methyl-2-pyrrolidone or dimethyl sulfoxide.

In a preferred embodiment of the invention the delivery system for forming an implant contains from about 10 wt % to about 50 wt % of a poly(lactide-co-glycolide) polymer (PLG or PLGH). The polymer is in a ratio of from 50/50 to 85/15 lactide to glycolide. This polymeric material has an inherent viscosity of from about 0.1 dL/g to about 0.4 dL/g. The delivery system further includes about 50 wt % to about 90 wt % of a biocompatible solvent, about 1 wt % to about 25 wt % of a bioactive agent and a sufficient amount of a stabilizing associate.

The following examples are intended to illustrate the features and scope of the invention and are not directed toward limiting the invention in any manner. The examples demonstrate the effect of a stabilizing associate in combination with the bioactive agent.

EXAMPLE 1

PLGH/NMP/Ocreotide Acetate/Citrate, Excess

The following composition was prepared. The composition was prepared to be dispensed as a two syringe, A/B product configuration. Syringe A (1.2 cc) contained about 244 mg of a solution composed of 37% by weight poly(lactide-co-glycolide) (PLG) with a lactide to glycolide ratio of 50/50 and with an inherent viscosity of 0.35 dL/g dissolved in 63% by weight N-methyl-2-pyrrolidone. Syringe B (1.2 cc) contained 30 mg of octreotide acetate/citrate combined with 6.8 mg of citric acid. The octreotide acetate/citrate is expressed as the amount of active peptide. The syringe B material was formed by dissolving the octreotide as octreotide acetate in water and then adding the citric acid to dissolve. The resulting solution was then filled into a syringe and the contents were lyophilized.

Prior to injection into a test organism, Syringe A and Syringe B were coupled and the final composition was constituted by expressing the contents of Syringe A into Syringe B. The resulting mixture was homogenized by cycling the contents between the two syringes for approximately 60 seconds. The final cycle placed the composition in Syringe B and Syringe A was decoupled. The needle for injection was attached to Syringe B and the composition was ready for administration.

The final composition for injection contained octreotide acetate/citrate at a concentration of 10.6% by weight, expressed as active peptide. The composition was physically stable upon compounding and was sufficiently stable upon injection into a test subject to form a controlled release implant. The delivered amount of composition to a test subject averaged approximately 180 mg, an amount containing approximately 20 mg of active octreotide. The sustained release of octreotide from the implant was maintained over a period of 30 days.

EXAMPLE 2

PLGH/NMP/Octreotide Citrate 1:1

The following composition was prepared. As in example 1 the composition is dispensed as a two syringe, A/B product configuration. Syringe A contained a solution composed of 50% by weight of poly(lactide-co-glycolide) (PLGH) with a lactide to glycolide ratio of 85/15 and with an inherent viscosity of 0.25 dL/g dissolved in 50% by weight N-methyl-2-pyrrolidone. Syringe B contained octreotide combined with citric acid in a molar ratio of 1:1. The syringe B material was formed by dissolving the octreotide as octreotide acetate in water and then adding the citric acid to dissolve. The resulting solution was then filled into a syringe and the contents were lyophilized to remove the water and acetic acid.

The syringes were coupled as in example 1 and the contents cycled to form the composition for injection. The composition contained octreotide at a concentration of 12% by weight. Corrected for active purity of the peptide, the solution contained active octreotide at a concentration of about 9.6% by weight. Following constitution, the composition showed sufficient stability for injection. Approximately 100 mg of the composition was injected into individual test animals, and the resulting implants displayed a controlled release of octreotide over period of 90 days.

Example 2 adjusted for human administration would consist of an approximate 90 mg dose of octreotide in about 750 mg of composition.

EXAMPLE 3

PLGH/NMP/GHRP-1/Citrate

The following composition was prepared. The polymer solution was composed of 50% by weight of poly(lactide-co-glycolide) (PLGH) with a lactide to glycolide ratio of 75/25 and with an inherent viscosity of 0.20 dL/g dissolved in 50% by weight N-methyl-2-pyrrolidone. The active portion was composed of GHRP-1 and citric acid. The ratio of citric acid to GHRP-1 was about 1.25:1 on a molar basis. The GHRP-1 was dissolved in water; citric acid was added to dissolve; and the solution was filled into a syringe and lyophilized. The contents of the completed syringe were about 80 mg of GHRP-1 and about 20 mg of citric acid.

For administration to a test subject, approximately 0.8 ml of composition was compounded. Syringe A containing the polymer solution was coupled with syringe B containing the GHRP-1, and the contents were cycled between the syringes to form a uniform composition. The completed composition contained GHRP-1 at a concentration of 100 mg/ml expressed as active peptide and citric acid at a concentration of 25 mg/ml. The composition showed the appearance of a stable mixture for injection. The delivered amount into the test subject was approximately 0.7 ml. The composition upon injection to a test animal formed an implant that resulted in a controlled delivery of GHRP-1 to the test subject over a period of 30 days.

EXAMPLE 4

Degradation of Polylactide-Glycolide by Octreotide Acetate

A solution of 34 wt % of 50/50 carboxyl terminated polylactide glycolide (PLGH at a 1:1 ratio of lactide to glycolide) in N-methylpyrrolidone (NMP) was prepared and divided into several aliquots. To a 950 mg aliquot was added 57.01 mg of octreotide acetate (OA) to provide a solution of 5.66 wt % octreotide acetate in a 34 wt % solution of PLGH in NMP. Upon standing at ambient temperature for 2 hours, the aliquot with OA and a control aliquot containing only PLGH and NMP were analyzed for average molecular weight of the PLGH by GPC analysis. The retention times were correlated against predetermined molecular weight standards of polylactide-glycolide which had been calibrated by GC-mass spectroscopy.

At the 2 hour mark, the control aliquot provided an average molecular weight measurement for the PLGH of 37,628 daltons while the OA aliquot provided an average molecular weight measurement for the PLGH of 20,173 daltons.

These data demonstrate that the octreotide causes significant degradation of the PLGH molecular weight even as the acetate salt.

EXAMPLE 5

Study of Polymer Decomposition in the Presence of Citrate Complexes of Octreotide A study of the decomposition rate of polylactide-glycolide in the presence of octreotide acetate-citrate complexes at various ratios was conducted.

A stock solution of 30 wt % of 50/50 polylactide-glycolide (PLGH, inherent viscosity 0.57 dL/g) in N-methylpyrrolidone (NMP) was prepared. To aliquots of this stock solution were added the octreotide acetate-citric acid (OAC) samples indicated on Table 1 so as to produce 5 wt % OAC in the PLGH/NMP aliquots. The polymer average molecular weight of PLGH in each of the aliquots was periodically determined over a period of 220 hours by GPC analysis using a set of pre-calibrated polylactide-glycolide average molecular weight standards to relate retention times to average molecular weight. The results are provided in the following graph, 1869-03. Table 1 provides the ratios of octreotide acetate (OA) to citric acid (C) that were examined. These data are also presented as a graph in FIG. 1. The Graph Designations are the symbols shown on FIG. 1.

| Graph Designation | Ingredients | Ratio of OA to C |
|---|---|---|
| ● | OAC | 0.5:1 |
| ○ | OAC | 1:1 |
| ▼ | OAC | 2:1 |
| ▲, clear | OAC | 3:1 |
| ■ | OAC | 1:1 physical mix, no soln. |
| ■, clear | OAC | 0.33:1 |
| ◊, filled | OAC | 0.25:1 |
| — | Baseline | |

EXAMPLE 6

Polymer Degradation by Octreotide Acetate, Solvent Study

A study of the influence of solvent upon the decomposition of polylactide-glycolide was conducted.

Portions of polylactide glycolide 50/50 having an inherent viscosity of 0.57 dL/g and an average molecular weight of 62,824 were dissolved in various solvents so as to provide 30 wt % solutions of the PLGH. The solvents examined included: N-methylpyrrolidone (NMP), acetone, ethyl acetate, 2-pyrrolidinone, pyrrolidine, pyrrole, pyridine. The average molecular weight of the PLGH in the various solutions was periodically determined over a period of 220 hours by GPC analysis using pre-calibrated polylactide-glycolide standards to relate retention times to average molecular weight. The following graph 1869-01 presents the results.

Figure 2:
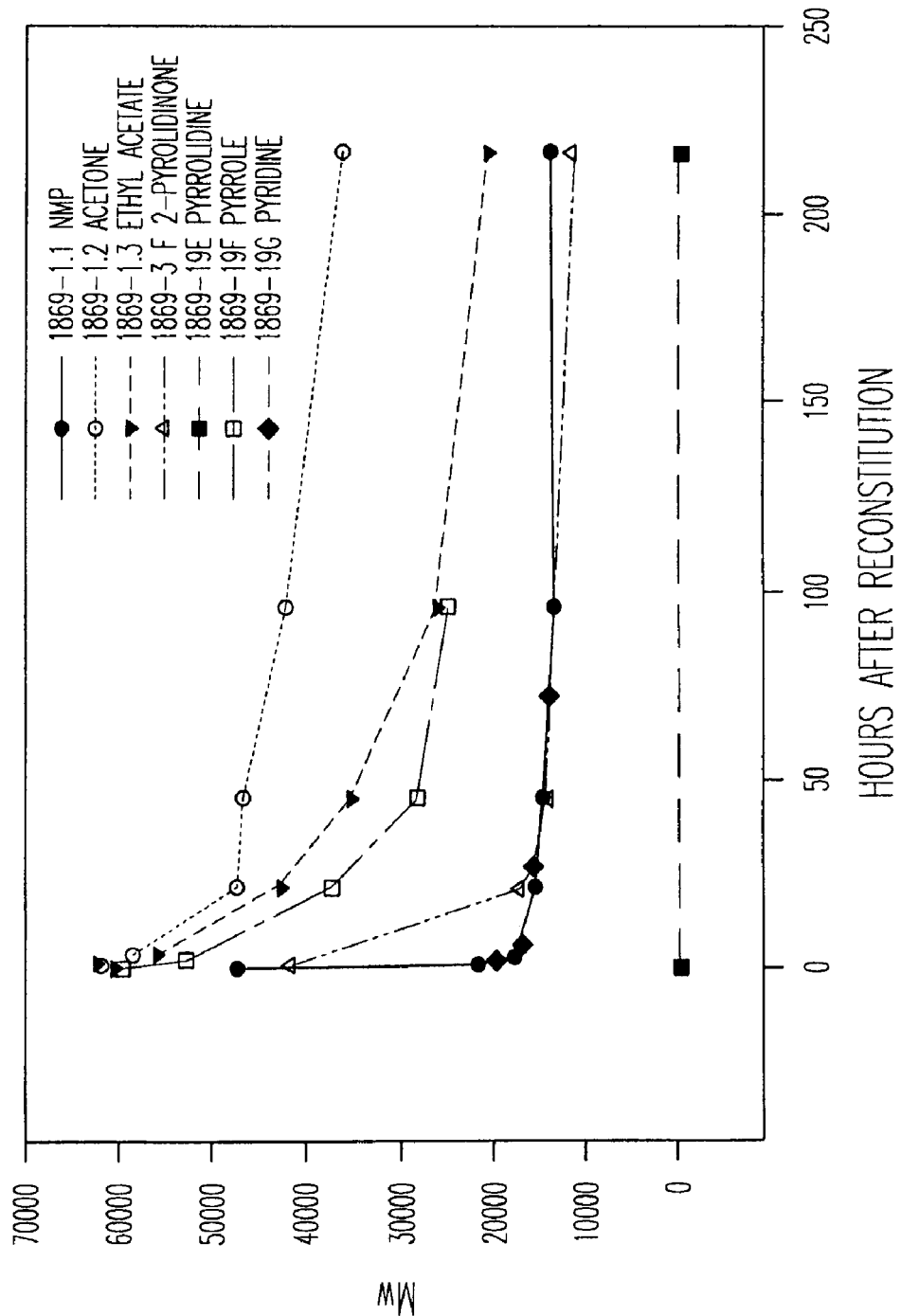
FIG. 2 is a graph showing the molecular weight degradation, over time, of polylactide glycolide in the presence of octreotide acetate and in the presence of various solvents.

The graph demonstrates that all solvents enable significant degradation of the PLGH. Those solvents having lower water solubility do not enable as high a degree of degradation as those solvents having high water solubility. The data determined by this experiment are presented graphically in FIG. 2.

EXAMPLE 7

Effect of Differing Octreotide Complexes on Decomposition of PLGH

A study of the effect of differing octreotide-citrate complexes upon the decomposition of polylactide/glycolide was conducted.

Figure 3:
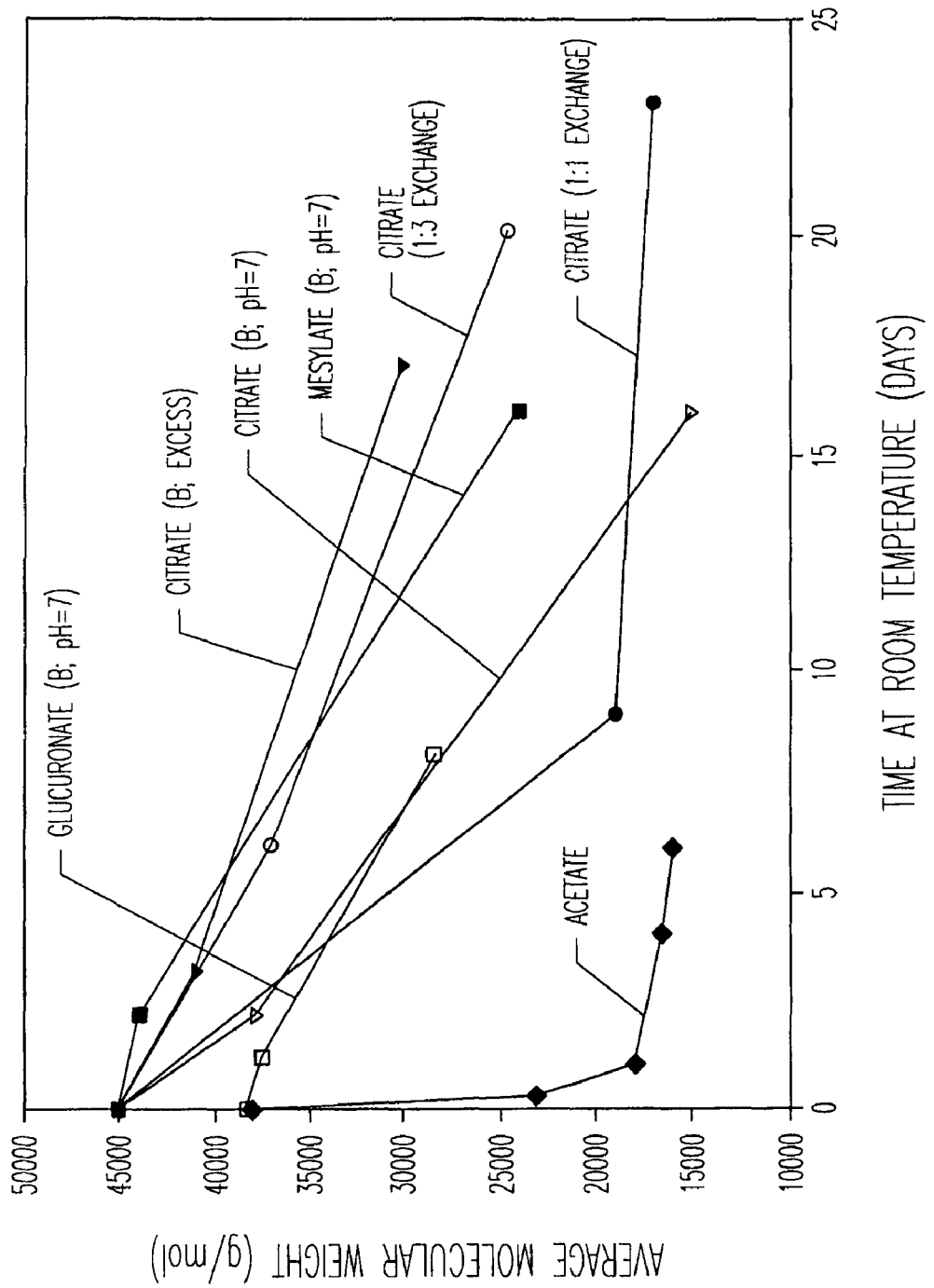
FIG. 3 is a graph showing the molecular weight degradation, over time, of polylactide glycolide in the presence of various octreotide salts.

Aliquots of a solution of 50/50 polylactide glycolide having an inherent viscosity of 0.57 dL/g and an average molecular weight of 45,000 were prepared so as to provide 35 wt % aliquots of the PLGH in N-methylpyrrolidone (NMP). To individual aliquots was added one of the following octreotide free base (OB)—complexes: OB-citrate; OB mesylate; OB-acetate; OB-Glucuronate. The OB-citrate complex was studied at several ratios: excess OB, 1:3 exchange, 1:1 exchange and citrate to pH 7. The average molecular weight of the PLGH in the solution was periodically determined over a period of 25 days by GPC analysis using pre-calibrated polylactide-glycolide standards for retention times. The following graph presents the results. The graph demonstrates that the acetate salt caused immediate dramatic degradation while citrate with excess octreotide base exhibited the lowest degree of degradation. The data determined by this experiment are presented graphically in FIG. 3.

EXAMPLE 8

Decomposition of PLGH in NMP

A study of the decomposition of polylactide/glycolide (PLGH) in N-methylpyrrolidone (NMP) was conducted.

Figure 4:
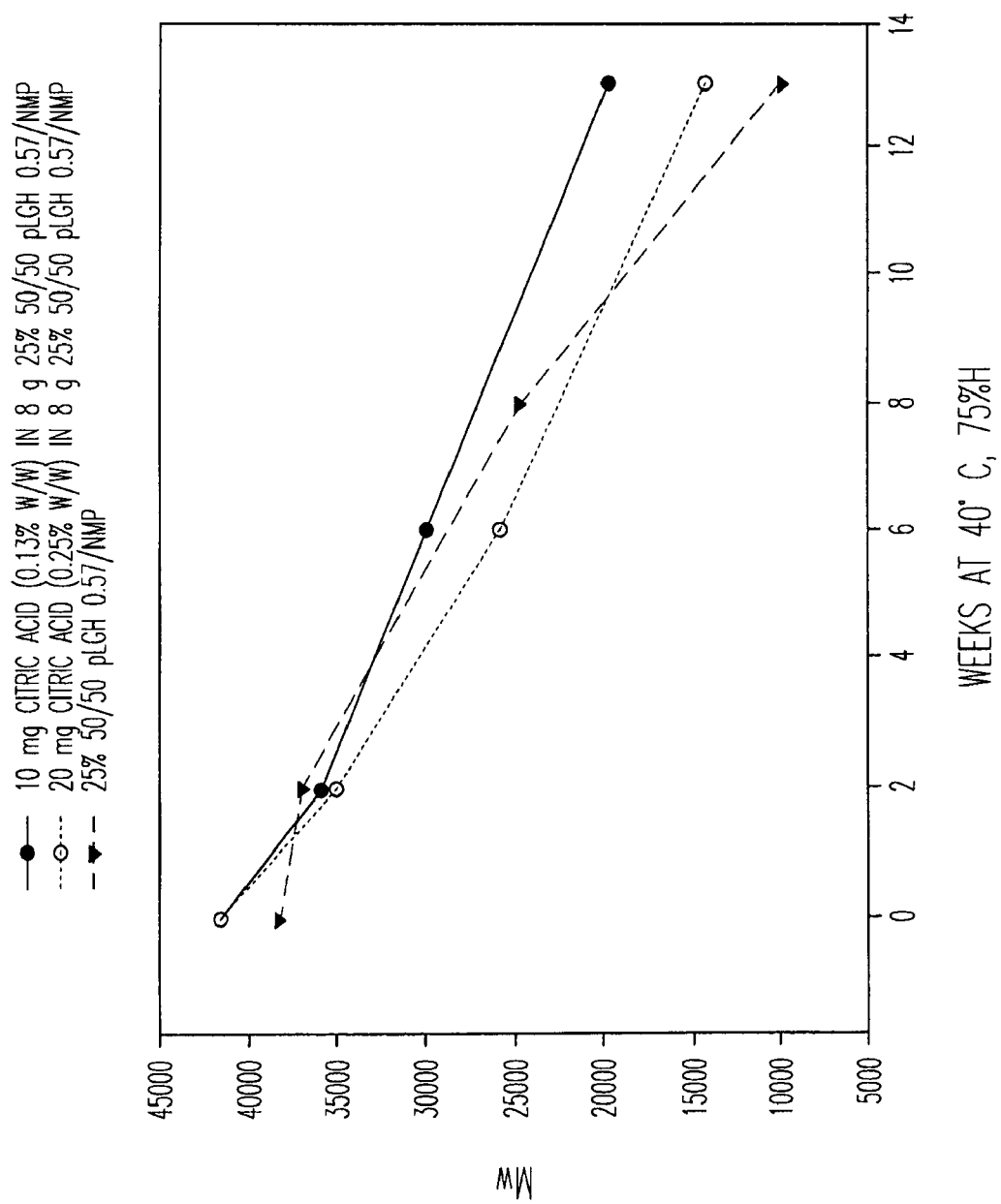
FIG. 4 is a graph showing the molecular weight degradation, over time, of polylactide glycolide in the presence and absence of citric acid but with no nucleophilic substance present.

Aliquots of a solution of 25 wt % 50/50 polylactide/glycolide (inherent viscosity of 0.57 dL/g) in NMP were prepared. Citric acid was added at 0.13 wt % and at 0.25 wt % to two of the aliquots and a third was maintained as a control. The average molecular weight of the PLGH in the solution was periodically determined over a period of 14 weeks by GPC analysis using pre-calibrated polylactide-glycolide standards for retention times. The following graph presents the results. The graph demonstrates that the average molecular weight of polylactide-glycolide in NMP decreases to approximately one-half of its original value over a period of 14 weeks. While this decomposition occurs in the absence of nucleophilic substances or acidic substances (such as citric acid), comparison of this period of degradation to those of the prior experiments shows that nucleophilic substances significantly increase the rate of PLGH degradation. The data determined by this experiment are presented graphically in FIG. 4.

EXAMPLE 9

Formulation Study for Clinical Evaluation

During several preclinical studies concerning a GHRP-1/ATRIGEL formulation, it was noted that commercial scale manufacture necessitated the standing of the citrate formulation which resulted in some precipitation of GHRP-1 from the GHRP-1/Citrate solution. When citric acid was added to the bulk solution, GHRP-1 tended to precipitate out of the solution over a couple of hours and made syringe filling difficult. Subsequent re-formulation studies showed that addition of a small amount of a solubilizing agent such as acetic acid to the bulk GHRP-1 citrate solution largely ameliorated this precipitation. This formulation was identified as AL3922.02. Subsequently, this formulation (AL3922.02) was found also to exhibit partial precipitation so as to enable commercial manufacture. Consequently, a fourth formulation (AL3922.04) was developed. The new formulation did not exhibit partial precipitation over the time needed for commercial formulation and exhibited similar in vivo release characteristics as the original formulation. Subsequently, the new formulation was slightly altered to produce version 2. Bulk version 2 was stable and did not exhibit precipitation. Version 2 was loaded into a syringe and the syringe contents lyophilized to remove water and acetic acid.

Table 1 summarizes the precipitation studies that were conducted for each formulation. The acronyms are identified as follows: GHRP-1 is a known pentapeptide mimicking growth hormone releasing peptide; DL2A is poly (DL) lactide-glycolide (75/25) having a terminal carboxyl group and an average molecular weight of about 13 kDa and an inherent viscosity of about 0.17 dL/g; NMP is N-methylpyrrolidone.

TABLE 1

Summary of GHRP-1 Formulations

| Code | Formulation | Comments |
|---|---|---|
| AL3922.01 | Syringe A:<br>80 mg active GHRP-1<br>18 mg citric acid<br>Syringe B:<br>926 mg 50% 7525<br>DL2A/50% NMP | Drug does not remain in solution long enough for commercial manufacturing. Syringeability (needle clogging) |
| AL3922.02 | Syringe A:<br>80 mg active GHRP-1<br>18 mg citric acid<br>2.0% acetic acid solution<br>Syringe B:<br>926 mg 50% 7525<br>DL2A/50% NMP | Addition of 2% acetic acid was insufficient to prevent drug precipitation. Syringeability (needle clogging) |
| A13922.03 | Syringe A:<br>80 mg active GHRP-1<br>Syringe B:<br>926 mg 49% 7525<br>DL2A/49% NMP/2% citric acid | Addition of citric acid to Syringe B accelerated polymer degradation. The polymer vehicle may not have 2 year shelf-life. Syringeability (needle clogging) |
| AL3922.04 | Syringe A:<br>80 mg active GHRP-1<br>10 mg citric acid<br>2.0% acetic acid solution<br>Syringe B:<br>926 mg 53% 7525<br>DL2A/47% INMP | Drug release comparable to AL3922.01.<br>A/B mixing sometimes difficult. Syringeability (needle clogging) |
| AL3922.04 Version 2 | Bulk Solution<br>7.8 wt% GHRP-1 in water<br>1.1 wt% citric acid<br>0.5 wt% acetic acid<br>Filled into syringe and lyophilized to remove water and acetic acid<br>Syringe A:<br>80 mg active GHRP-1<br>11 mg citric acid<br>Syringe B:<br>50% DL2A in NMP | Product readily injectable through syringe needle |

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A composition comprising a biodegradable, biocompatible, essentially water-insoluble, thermoplastic polyester; a stabilizing associate that is a polycarboxylic acid; a nucleophilic bioactive agent having at least one nucleophilic nitrogen group in a free base or salt form, wherein the bioactive agent is a peptide, oligopeptide, polypeptide or protein; and an organic liquid, the composition being in the form of a flowable composition.

2. The composition of claim 1 wherein the biodegradable, biocompatible thermoplastic polymer polyester is a linear polymer, or is a branched polymer.

3. The composition of claim 1 wherein the biodegradable, biocompatible thermoplastic polyester is selected from the group of polylactides, polyglycolides, polycaprolactones, polyhydroxybutyrates, polyorthoesters, copolymers thereof, block copolymers thereof, terpolymers thereof, and mixtures thereof.

4. The composition of claim 1 wherein the biodegradable, biocompatible thermoplastic polyester comprises monomeric units of one or more hydroxycarboxylic acids and a diol monomeric unit.

5. The composition of claim 1 wherein the polyester comprises monomeric units of one or more hydroxycarboxylic acids; or comprises monomeric units of one or more dicarboxylic acids and one or more diols.

6. The composition of claim 1 wherein the biodegradable, biocompatible thermoplastic polyester is at least one of a polylactide, a polyglycolide, a polycaprolactone, a copolymer thereof, a terpolymer thereof, or any combination thereof.

7. The composition of claim 1 wherein the biodegradable, biocompatible thermoplastic polyester is a poly(DL-lactide-co-glycolide); and has a carboxy terminal group; or is without a carboxy terminal group and contains a diol moiety.

8. The composition of claim 1 wherein the biodegradable, biocompatible thermoplastic polyester is present at about 20 wt. % to about 80 wt. % of the composition.

9. The composition of claim 1 wherein the biodegradable, biocompatible thermoplastic polyester has an average molecular weight of about 5,000 to about 100,000.

10. The composition of claim 1 wherein the biocompatible organic liquid has a water solubility ranging from completely insoluble in water in any proportion to completely soluble in all proportions in water, or the biocompatible organic liquid has a solubility parameter in a fluid selected from the group consisting of water, aqueous medium and body fluid, and the solubility parameter is any one of the conditions: insoluble, immiscible, slightly soluble, moderately soluble, soluble and completely soluble in all proportions.

11. The composition of claim 1 wherein the biocompatible organic liquid is a polar protic liquid or a polar aprotic liquid.

12. The composition of claim 1 wherein the biocompatible organic liquid is a cyclic, aliphatic, linear aliphatic, branched aliphatic or aromatic organic compound that is liquid at ambient and physiological temperature and contains at least one functional group selected from the group consisting of alcohol, ketone, ether, amide, amine, alkylamine, ester, carbonate, sulfoxide, sulfone and sulfonate.

13. The composition of claim 1 wherein the biocompatible organic liquid is N-methyl-2-pyrrolidone, 2-pyrrolidone, N,N-dimethylformamide, dimethyl sulfoxide, propylene carbonate, caprolactam, triacetin, benzyl benzoate or any combination thereof.

14. The composition of claim 1 wherein the biocompatible liquid is present at about 30 wt. % to about 80 wt. % of the composition.

15. The composition of claim 1 wherein the biocompatible liquid is dispersible in at least one of aqueous medium, water, or body fluid but is not dispersible in all of the medium, water and body fluid.

16. The composition of claim 1 further comprising a component selected from the group consisting of a release rate modification agent for controlling the rate of release of the bioactive agent in vivo from an implant matrix; a pore-forming agent; a biodegradable, crystallization-controlling agent; a plasticizer; a leaching agent; a penetration enhancer; an absorption altering agent; a colorant; a solubilizing agent; or any combination thereof.

17. The composition of claim 1, wherein the composition is capable of forming a solid microporous matrix when contacted by water, an aqueous medium or body fluid, the matrix being a core surrounded by a skin and the core containing pores of diameters from about 1 to about 1000 microns; and the skin contains pores of smaller diameters than those of the core.

18. The composition of claim 1 having a volume of about 0.20 mL to about 0.50 mL.

19. A method of forming an in situ implant in a mammal, comprising administering to a mammal in need of such treatment, an effective amount of the composition of claim 1.

20. A solid implant comprising: a biodegradable, biocompatible, thermoplastic water-insoluble polyester, a stabilizing associate that is a polycarboxylic acid; and a bioactive agent having at least one nucleophilic nitrogen group in a free base or salt form, wherein the bioactive agent is a peptide, oligopeptide, polypeptide or protein; and wherein the solid implant is formed by contact of the composition of claim 1 with an aqueous medium, or body fluid within the tissue of a living patient.

21. An implant comprising the composition of claim 1.

22. The implant according to claim 20 or 21, wherein the implant is positioned within the tissue of a mammal.

23. The implant according to claim 20 or 21 wherein the implant has a solid porous matrix.

24. The implant of claim 21 wherein the thermoplastic polymer is partially solidified, or alternatively, the thermoplastic polymer is fully solidified, or alternatively, the amount of biocompatible organic liquid decreases over time.

25. The implant of claim 21 wherein the organic liquid is completely insoluble in water, is slightly soluble in water, is moderately soluble in water, is soluble in water or is completely soluble in water in all proportions.

26. A method of forming a solid implant in situ within a living body, comprising:
(a) injecting the flowable composition of claim 1 into the body of a patient; and
(b) allowing the biocompatible organic liquid to dissipate to produce a solid biodegradable implant.

27. A pharmaceutical kit suitable for in situ formation of a biodegradable implant in a body, the kit comprising:
(a) a container containing at least the flowable composition of claim 1 wherein the container is a syringe.

28. A method of administering to a mammal a bioactive agent having at least one nucleophilic nitrogen group in free base or salt form comprising inserting into the mammal the composition of claim 1.

29. The composition of claim 1 wherein the polycarboxylic acid comprises a di, tri or tetra carboxylic acid of 2 to 100 carbons.

30. The composition of claim 29 wherein the di or tri carboxylic acid is a di carboxylic acid of 2 to 10 carbons or a tri carboxylic acid of 4 to 15 carbons; and optionally, the di or tri carboxylic acid also is substituted by hydroxyl groups.

31. The composition of claim 1 which has the property of flowability when it is not in contact with aqueous medium, body fluid or liquid water.

32. The composition of claim 13 wherein the organic liquid is N-methyl-2-pyrrolidone.

* * * * *